US010473506B1

(12) United States Patent
Salerno

(10) Patent No.: US 10,473,506 B1
(45) Date of Patent: *Nov. 12, 2019

(54) OIL LEVEL VISUALIZATION SYSTEM

(71) Applicant: Douglas Joseph Salerno, Lebanon, TN (US)

(72) Inventor: Douglas Joseph Salerno, Lebanon, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/056,051

(22) Filed: Aug. 6, 2018

Related U.S. Application Data

(63) Continuation-in-part of application No. 15/215,342, filed on Jul. 20, 2016, now Pat. No. 10,066,978.

(60) Provisional application No. 62/195,664, filed on Jul. 22, 2015, provisional application No. 62/216,170, filed on Sep. 9, 2015, provisional application No. 62/246,202, filed on Oct. 26, 2015.

(51) Int. Cl.
G01F 23/04 (2006.01)
G01N 1/28 (2006.01)

(52) U.S. Cl.
CPC ..... *G01F 23/04* (2013.01); *G01N 2001/2826* (2013.01)

(58) Field of Classification Search
CPC .................................. G01F 23/22; G01F 23/04
USPC ............................................................ 33/701
See application file for complete search history.

(56) References Cited

U.S. PATENT DOCUMENTS

| | | | | | |
|---|---|---|---|---|---|
| 2,176,618 | A | * | 10/1939 | Wilson | F16N 29/04 356/70 |
| 2,224,123 | A | * | 12/1940 | Wilson | G01N 21/293 356/70 |
| 2,507,684 | A | * | 5/1950 | Smith | G01B 3/02 33/758 |
| 2,705,372 | A | * | 4/1955 | Cornell | G01F 23/04 33/726 |
| 2,764,294 | A | * | 9/1956 | Johnson | G01F 23/04 210/222 |
| 4,024,989 | A | * | 5/1977 | Wessely | B67C 9/00 222/154 |
| 4,351,183 | A | * | 9/1982 | Egbert | G01N 13/04 73/32 R |
| 4,480,718 | A | * | 11/1984 | Marinelli | F01M 11/12 184/1.5 |
| 4,720,997 | A | * | 1/1988 | Doak | G01F 23/246 327/512 |
| 4,988,975 | A | * | 1/1991 | Nap | G01F 23/04 324/696 |
| 5,072,625 | A | * | 12/1991 | Anderson | G01F 23/0046 33/717 |
| 6,001,658 | A | * | 12/1999 | Fredrickson | G01N 33/558 422/402 |
| 6,981,335 | B1 | * | 1/2006 | Darden | G01F 23/04 33/722 |

(Continued)

*Primary Examiner* — Yaritza Guadalupe-McCall
(74) *Attorney, Agent, or Firm* — Shane Cortesi

(57) ABSTRACT

The present invention relates to oil level visualization system that is used in place of a conventional dipstick to measure oil level. The system may include a strip that has a tube attached thereto comprising an oil absorbent material. Oil from the oil reservoir is configured to absorb to the oil absorbent material and absorbing of the oil to the oil absorbent material is configured to provide a stain on the oil absorbent material visible to the naked eye. The present invention also relates to methods of using the same.

20 Claims, 30 Drawing Sheets

(56) References Cited

U.S. PATENT DOCUMENTS

| | | | | |
|---|---|---|---|---|
| 7,360,319 B1* | 4/2008 | Goldstein | ............... | G01F 23/04 15/220.4 |
| 7,418,788 B1* | 9/2008 | Herr | ........................ | G01F 23/04 33/722 |
| 7,578,071 B2* | 8/2009 | Goldstein | ............... | G01F 23/04 33/725 |
| 10,066,978 B1* | 9/2018 | Salerno | ................... | G01F 23/04 |
| 2008/0216858 A1* | 9/2008 | Goldstein | ............... | G01F 23/04 132/218 |
| 2013/0224408 A1* | 8/2013 | Malloy | ................... | G01F 23/04 428/35.2 |
| 2015/0047429 A1* | 2/2015 | Ha | ........................ | G01F 23/22 73/292 |

\* cited by examiner

OIL LEVEL VISUALIZATION SYSTEM

RELATED APPLICATIONS

This application is a continuation-in-part of U.S. patent application Ser. No. 15/215,342, filed Jul. 20, 2016. U.S. patent application Ser. No. 15/215,342 claims priority under 35 USC 119 to U.S. Provisional Application No. 62/195,664, filed Jul. 22, 2015, to U.S. Provisional Application No. 62/216,170, filed Sep. 9, 2015, and U.S. Provisional Application No. 62/246,202, filed Oct. 26, 2015. The entire contents of the all of the above are incorporated by reference in their entirety.

BACKGROUND

Technical Field

The present invention relates to oil level visualization systems.

Background of the Invention

Dipsticks are commonly used to measure oil levels in car engines, lawn mower engines and other engines. As known to those of ordinary skill, engine oil level is typically read by an individual removing a metal dipstick from the oil reservoir, wiping the oil off the dipstick, re-inserting the dipstick into the reservoir, removing the dipstick from the reservoir, and then observing the oil level on the dipstick in reference to a marker, e.g., raised indicia on the dipstick. Visualizing oil level on the dipstick was much easier years ago, when oil was darker. However, most of the oil used today is clearer, slicker, and very hard to visualize on a dipstick.

U.S. Pat. No. 7,418,788 teaches a method for determining transmission oil level by using a thermochromic plastic billet secured to a dipstick. The thermochromic plastic is configured to change colors when the transmission oil is at a desired temperature, namely, 150 degrees Fahrenheit (65 degrees Celsius). The system of the aforementioned patent is not designed to be used when the oil is at ambient temperature (because among other things the thermochromic material would not change color). In addition, plastics generally do not absorb oil, and thermochromic plastics may be more costly than the present invention.

Thus, there is a continuing need for easy to make and use methods for visualizing oil level in an engine, especially for methods that are not dependent on oil temperature and may be undertaken when the oil is at ambient temperature (e.g., a typical oil change).

BRIEF SUMMARY

The present disclosure provides a dipstick visualization system as described herein. In some embodiments, the system includes: a) an engine comprising an oil reservoir configured to hold oil; b) a dipstick configured to be disposed in the oil reservoir and measure oil level in the oil reservoir; c) a strip comprising a front surface comprising an oil absorbent material and a rear surface configured to confront the dipstick; and d) a fastener configured to removably attach the oil absorbent material (more particularly the strip) to the dipstick, wherein oil from the oil reservoir is configured to absorb to the oil absorbent material and absorbing of the oil to the oil absorbent material is configured to provide a stain on the oil absorbent material visible to the naked eye.

Optionally, the fastener is selected from the group consisting of an adhesive sticker, a clip, and a magnet. Optionally, the fastener is an adhesive sticker and the adhesive sticker is located on the rear surface of the strip. Optionally, the adhesive sticker comprises an adhesive and a removable paper or paper-based backing configured to cover the adhesive until the adhesive confronts the dipstick. Optionally, the strip comprises a top end, a bottom end, a length extending from the top end to the bottom end, at least one pull tab located at an end of the strip, the at least one pull tab having a rear surface designed to confront the dipstick. Optionally, the oil absorbent material is comprised of a cellulosic material, such as paper or paper-based material, e.g., paper board and paper cardstock, and the cellulosic material forms all or substantially all of the front surface of the strip. Optionally, the oil absorbent material is comprised of cloth. Optionally, the oil absorbent material is comprised of felt. Optionally, the strip front surface is comprised of a paper-based material, preferably paper board or paper cardstock. Optionally, the strip rear surface is comprised of brass and the strip front surface is comprised of a paper-based material. Optionally, oil in the oil reservoir is configured to absorb to the oil absorbent material at ambient temperature and absorbing of the oil to the oil absorbent material is configured to provide a stain visible to the naked eye at ambient temperature. Optionally, oil in the oil reservoir is configured to absorb to the oil absorbent material independent of the oil temperature and absorbing of the oil to the oil absorbent material is configured to provide a stain visible to the naked eye. Optionally, the strip has a top end, a bottom end, a length extending from the top end to the bottom end of from about 1 inch to about 1¾ inches and a width perpendicular to the length of from about 3/16 inches to about 5/16 inches. Optionally, the strip width is wider at the top end and at the bottom end. Optionally, the strip comprises at least one indicia. Optionally, the dipstick is comprised of metal The present disclosure also provides a method of using an oil level visualization system comprising: a) providing an engine comprising an oil reservoir configured to hold oil; b) providing a dipstick configured to be disposed in the oil reservoir and measure oil level in the oil reservoir; c) providing an oil absorbent material comprising a rear surface configured to confront the dipstick; d) providing a fastener configured to removably attach the oil absorbent material to the dipstick; e) using the fastener to removably attach the oil absorbent material to the dipstick; and f) absorbing oil from the oil reservoir to the oil absorbent material to provide a stain on the oil absorbent material visible to the naked eye.

Optionally, the method further includes: g) removing the oil absorbent material from the dipstick.

In still further embodiments, the present disclosure provides a method of using an oil level visualization system comprising: a) providing an engine comprising an oil reservoir configured to hold oil, the oil reservoir comprising a dipstick configured to measure oil level in the oil reservoir; b) removing the dipstick from the oil reservoir; c) providing a strip comprising a backing and an oil absorbent material, the strip having a top end, a bottom end, a length extending from the top end to the bottom end, and a width perpendicular to the length; d) inserting the strip into the oil reservoir; and e) absorbing oil from the oil reservoir to the oil absorbent material to provide a stain on the oil absorbent material visible to the naked eye.

Optionally, the method further comprises drawing at least one line on the oil absorbent material prior to step d). Optionally, the method further comprises drawing a plurality of lines on the oil absorbent material prior to step d). Optionally, at least one of the plurality of lines is adjacent to the top end. Optionally, the oil absorbent material is comprised of a cellulosic material. Optionally, the oil absorbent material is comprised of paper cardstock or paper board. Optionally, the strip is capable of being bent by a user with his/her hands. Optionally, the method further comprises the step of f) removing the strip from the oil reservoir. Optionally, the method further comprises the step of bending the top end relative to the bottom end prior to step d). Optionally, oil in the oil reservoir is configured to absorb to the oil absorbent material at ambient temperature and absorbing of the oil to the oil absorbent material is configured to provide a stain visible to the naked eye at ambient temperature. Optionally, oil in the oil reservoir is configured to absorb to the oil absorbent material independent of the oil temperature and absorbing of the oil to the oil absorbent material is configured to provide a stain visible to the naked eye. Optionally, the strip comprises a thickness perpendicular to the strip length and strip width and further wherein the thickness is from about 0.015 inches to about 0.3 inches. Optionally, the backing is metallic or plastic. Optionally, the strip further comprises a double-sided adhesive located between the backing and oil absorbent material, the double-sided adhesive securing the oil absorbent material to the backing. Optionally, the top end of the strip is rolled to create a handle. Optionally, the handle is generally circular in shape. Optionally, the length of the strip is from about 4 inches to about 35 inches and further wherein width of the strip is from about 0.15 inches to about 0.5 inches. Optionally, the length of the strip is from about 20 inches to about 35 inches.

In still further embodiments, the present disclosure provides a method of using an oil level visualization system comprising: a) providing an engine comprising an oil reservoir configured to hold oil, the oil reservoir comprising a dipstick configured to measure oil level in the oil reservoir; b) removing the dipstick from the oil reservoir; c) providing a strip comprising an oil absorbent material, the strip having a top end, a bottom end, a length extending from the top end to the bottom end, a left side, a right side and a width extending from the left side to the right side and perpendicular to the length; d) inserting the strip into the oil reservoir; and e) absorbing oil from the oil reservoir to the oil absorbent material to provide a stain on the oil absorbent material visible to the naked eye.

Optionally, the method further comprises drawing at least one line on the oil absorbent material prior to step d). Optionally, the method further comprises drawing a plurality of lines on the oil absorbent material prior to step d). Optionally, at least one of the plurality of lines is adjacent to the top end. Optionally, at least one of the plurality of lines is adjacent to the bottom end. Optionally, the oil absorbent material is comprised of a cellulosic material. Optionally, the oil absorbent material is comprised of paper cardstock or paper board. Optionally, the strip consists essentially of paper cardstock or paper board. Optionally, the strip is capable of being bent by a user with his/her hands. Optionally, the method further comprises the step of f) removing the strip from the oil reservoir. Optionally, the method further comprises the step of bending a segment of the strip relative to the bottom end prior to step d). Optionally, after bending, the segment is generally perpendicular to the remainder of the strip. Optionally, oil in the oil reservoir is configured to absorb to the oil absorbent material at ambient temperature and absorbing of the oil to the oil absorbent material is configured to provide a stain visible to the naked eye at ambient temperature. Optionally, oil in the oil reservoir is configured to absorb to the oil absorbent material independent of the oil temperature and absorbing of the oil to the oil absorbent material is configured to provide a stain visible to the naked eye. Optionally, the strip comprises a front surface, a rear surface, a thickness extending from the front surface to the rear surface, the thickness perpendicular to the strip length and strip width and further wherein the thickness is from about 0.05 inches to about 0.3 inches. Optionally, the top end of the strip is rolled to create a handle. Optionally, the handle is generally circular in shape. Optionally, the length of the strip is from about 4 inches to about 35 inches. Optionally, the strip comprises a variable width. Optionally, the left side of the strip comprises a left indentation adjacent to the bottom end of the strip and the right side of the strip comprise right indentation adjacent to the bottom end of the strip, the left indentation comprising a left indentation top end, a left indentation bottom end, and a left indentation length extending from the left indentation top end to the left indentation bottom end, the right indentation comprising a right indentation top end, a right indentation bottom end, and a right indentation length extending from the right indentation top end to the right indentation bottom end, the left indentation top end, the left indentation bottom end, the right indentation top end and the right indentation bottom end defining a tapered segment of the strip. Optionally, the distance from the left indentation top end to the right indentation top end is from about 0.05 to about 0.25 less than the width of the strip directly above the left indentation top end and the right indentation. Optionally, the distance from the left indentation top end to the right indentation top end is between about 0.1 to about 0.2 inches and further wherein the width of the strip directly above the left indentation top end and the right indentation top end is from about 0.15 inches to about 0.35 inches. Optionally, the method further comprises drawing at least one line on the oil absorbent material in the tapered segment prior to step d). Optionally, the oil reservoir further comprises a dipstick tube and further wherein the method further comprises wiping a segment of the strip adjacent the tapered segment against a side of the dipstick tube during step d) and after step e) (i.e., both while inserting the strip into the oil reservoir and removing the strip from the oil reservoir). Optionally, the left indentation and the right indentation are generally rectangular in shape. Optionally, the length of the strip is from about 20 inches to about 35 inches.

In still further embodiments, the present disclosure provides a method of using an oil level visualization system comprising:

a) providing a dipstick package comprising:

i) a package backing comprising a package backing front surface, a package backing rear surface, a package backing top end, a package backing bottom end, a package backing length extending from the package backing top end to the package backing bottom end, a package backing left side, a package backing right side, and a package backing width extending from the package backing left side to the package packing right side;

ii) a plurality of adjacent strips located on the package backing front surface, each of the plurality of adjacent strips contacting the package backing front surface, each of the plurality of adjacent strips comprising an oil absorbent material, a top end, a bottom end, a length extending from the top end to the bottom end, a left side, a right side, and a width extending from the left side to the right side, the width of the plurality of adjacent strips generally parallel to the package backing width and the length of the plurality of adjacent strips generally parallel to the package backing length;

iii) a plurality of slots located between adjacent sides of adjacent strips and partially separating adjacent strips, each slot having a slot length generally parallel to the strip length, the plurality of slots located in front of the backing front surface;

iv) a plurality of bridges connecting adjacent strips, each bridge integral with the strips connected by the bridge and comprised of the same material as the strips connected by the bridge, each bridge interrupting a slot; and v) a fastener connecting the plurality of adjacent strips to the package backing;

b) separating a strip from the other strips and the package backing;

c) providing an engine comprising an oil reservoir configured to hold oil, the oil reservoir comprising a dipstick configured to measure oil level in the oil reservoir;

d) removing the dipstick from the oil reservoir;

e) inserting the strip separated from the other strips and the package backing into the oil reservoir; and f) absorbing oil from the oil reservoir to the oil absorbent material of the strip separated from the other strips and the package backing to provide a stain on the oil absorbent material visible to the naked eye.

Optionally, the fastener is a cord. Optionally, the cord passes through at least two of the slots. Optionally, the cord passes through at least two fastener holes in the package backing, the at least two fastener holes extending from the package backing front surface to the package backing rear surface. Optionally, the method further comprises drawing at least one line on the oil absorbent material of the plurality of adjacent strips prior to step b). Optionally, the at least one line is generally parallel to the widths of the plurality of strips and to the package backing width. Optionally, the package backing width is greater than the combined width of the plurality of adjacent strips. Optionally the package backing length is greater than the length of each of the plurality of adjacent strips. Optionally, the package backing further comprises a hanger hole extending from the package backing front surface to the package backing rear surface.

In still further embodiments, the present disclosure provides a method of using an oil level visualization system comprising: a) providing an engine comprising an oil reservoir configured to hold oil, the oil reservoir comprising a dipstick configured to measure oil level in the oil reservoir; b) removing the dipstick from the oil reservoir; c) providing a strip having a top end, a bottom end, a length extending from the top end to the bottom end, a width perpendicular to the length, and a thickness perpendicular to the width and the length; d) providing a tube comprised of an oil absorbent material, the tube comprising a hollow interior receiving the strip (the tube may be positioned on the strip by the user or may be supplied already attached from the manufacturer); e) inserting at least the bottom end of the strip and the tube into the oil reservoir; and f) absorbing oil from the oil reservoir to the tube to provide a stain on the tube visible to the naked eye.

Optionally, the strip and the tube are comprised of different materials. For example, the strip may be comprised of a heat-resistant, non-oil absorbent material (e.g., plastic), and the oil absorbent material forming the tube may be a cellulosic material (e.g., a paper-based material). Optionally, prior to step e) the tube comprises at least one indicia visible to the naked eye, the indicia configured to provide a reading on the oil level in the reservoir to a user. Optionally, step e) comprises inserting the bottom end of the strip before the tube into the oil reservoir. Optionally, the strip comprises a bottom flange adjacent to the bottom end, the tube comprises a tube width parallel to the strip width and a tube thickness parallel to the strip thickness, the bottom flange comprises a bottom flange width parallel to the strip width and a bottom flange thickness parallel to the strip thickness and the bottom flange width is greater than the tube width and the bottom flange thickness is greater than the tube thickness. Optionally, the bottom flange is rounded and thus it will be understood that the aforementioned bottom flange width and thickness refer to the maximum width and thickness of the bottom flange. Optionally, the bottom flange is integral to the strip. Optionally, after step d), the method further comprises sliding a tube stop comprising a tube stop slot from the strip top end toward the tube and the strip bottom end, and further wherein the tube stop comprises a fastener configured to attach the tube stop to the strip. (The slot of the tube stops receive the strips and is preferably located in the center of the tube stop width and extends along the length of the tube stop). Optionally, the strip comprises a plurality of teeth spaced along the strip length and the tube stop fastener comprises a ratchet configured to engage the plurality of teeth and allow the tube stop to travel towards the tube and the bottom end of the strip. Optionally, the ratchet of the tube stop is configured to prevent the tube stop from traveling towards the top end of the strip. Optionally, the tube comprises a tube width parallel to the strip width and a tube thickness parallel to the strip thickness, wherein the tube stop comprises a tube stop width parallel to the strip width and a tube stop thickness parallel to the strip thickness and further wherein the tube stop width is greater than the tube width and further wherein the tube stop thickness is greater than the tube thickness. Optionally, the tube is generally cylindrical in shape and the tube stop comprises a flat bottom end configured to contact the tube and a rounded top end and the tube stop tapers from the tube bottom end to the tube top end. Thus, the recited tube stop width and thickness refers to the maximum tube stop width and thickness. Optionally, wherein the method further comprises sliding a top flange having a slot from the strip top end toward the tube prior to step e). (The top flange slot receives the strip and is preferably located in the center of the top flange width and extends along the length of the top flange). Optionally, the top end of the strip and the top flange are not inserted in the oil reservoir during steps a)-f). (Optionally, the width and thickness of top flange are greater than the width and thickness of the strip, excluding the bottom flange, so that the top flange is bigger than the top of the oil reservoir—e.g., the top of the dipstick tube). Optionally, the strip comprises a plurality of teeth spaced along the strip length and the top flange comprises a ratchet configured to engage the plurality of teeth and allow the top flange to travel towards the bottom end of the strip. Optionally, the ratchet of the top flange is configured to prevent the top flange from traveling towards the top end of the strip. Optionally, the user places his fingers between the top end of the strip and the top flange during steps e)-f). Optionally, oil in the oil reservoir is configured to absorb to the tube at ambient temperature. Optionally, oil in the oil reservoir is configured to absorb to the tube independent of the oil temperature.

The present disclosure also provides a method of using an oil level visualization system comprising: a) providing an engine comprising an oil reservoir configured to hold oil, the oil reservoir comprising a dipstick configured to measure oil level in the oil reservoir; b) removing the dipstick from the oil reservoir; c) providing a strip having a top end, a bottom end, a length extending from the top end to the bottom end, a width perpendicular to the length, and a thickness perpendicular to the width and the length; d) providing an oil absorbent material attached to the strip, the oil absorbent material comprised of a material different than the material comprising the strip; e) inserting at least the bottom end of the strip and the oil absorbent material into the oil reservoir; and f) absorbing oil from the oil reservoir to the oil absorbent material to provide a stain on the oil absorbent material visible to the naked eye.

The oil absorbent material may be in the form of the aforementioned tube and the system may further include one or more features of the prior embodiment, such as the bottom flange, the top flange, and the tube stop as well as the ratchets.

The present disclosure also provides an oil level visualization system comprising: a) a strip comprised of a heat-resistant, non-oil absorbent material and having a top end, a bottom end, a length extending from the top end to the bottom end, a width perpendicular to the length, and a thickness perpendicular to the width and the length; b) a plurality of teeth spaced about the strip length; c) a tube comprised of an oil absorbent material, the tube comprising a hollow interior receiving the strip, a tube width parallel to the strip width and a tube thickness parallel to the strip thickness, the tube width greater than the strip width and the tube thickness greater than the strip thickness, the tube comprised of a different material than the strip; d) a rounded bottom flange fixed to the strip bottom end and comprising a bottom flange width parallel to the strip width and a bottom flange thickness parallel to the strip thickness and further wherein the bottom flange width is greater than the tube width and further wherein the bottom flange thickness is greater than the tube thickness; e) a tube stop located between the tube and the strip top end, the tube stop comprising a tube stop ratchet configured to engage the plurality of teeth and allow the tube stop to travel towards the tube and the bottom end of the strip, the tube stop comprising a tube stop width parallel to the strip width and a tube stop thickness parallel to the strip thickness and further wherein the tube stop width is substantially the same size as the bottom flange width and the tube stop thickness is substantially the same size as the bottom flange thickness; and f) a top flange located between the tube stop and the top end of the strip, the top flange comprising a top flange ratchet configured to engage the plurality of teeth and allow the top flange to travel towards the tube stop, the tube and the bottom end of the strip.

In still further embodiments, the present disclosure provides: A method of using an oil level visualization system comprising: a) providing an engine comprising an oil reservoir configured to hold oil, the oil reservoir comprising a dipstick configured to measure oil level in the oil reservoir; b) removing the dipstick from the oil reservoir; c) providing a strip having a top end comprising a loop, a bottom end, a length extending from the top end to the bottom end, a width perpendicular to the length, and a thickness perpendicular to the width and the length, wherein a tube located below the loop is attached to the strip, the tube comprised of an oil absorbent material and comprising a hollow interior receiving the strip; d) inserting at least the bottom end of the strip and the tube into the oil reservoir; and e) absorbing oil from the oil reservoir to the tube to provide a stain on the tube visible to the naked eye.

Optionally, the strip is comprised of a heat-resistant, non-oil absorbent material. Optionally, the oil absorbent material is a cellulosic material (e.g., a paper-based material). Optionally, prior to step d) the tube comprises at least one indicia visible to the naked eye, the indicia configured to provide a reading on the oil level in the oil reservoir to a user. Optionally, the at least one indicia comprises a lower dimple located above the strip bottom end. Optionally, the strip comprises a front surface and a rear surface, wherein the thickness extends from the front surface to the rear surface, wherein the lower dimple is located on the front surface of the strip, and further wherein the rear surface of the strip comprises a bump located directly to the rear of the lower dimple. Optionally, the at least one indicia further comprises an upper dimple located above the lower dimple. Optionally, step d) comprises inserting the bottom end of the strip before the tube into the oil reservoir. Optionally, the strip is the form of a cable tie comprising a plurality of teeth spaced along the length of the strip and a ratchet configured to engage the plurality of teeth, the ratchet forming a bottom end of the loop and located above the tube. Optionally, the loop comprises an adjustable size and further wherein moving the ratchet upwardly reduces the size of the loop and increases the distance between the ratchet and the strip bottom end. Optionally, prior to step d) the tube comprises at least one indicia visible to the naked eye, the at least one indicia configured to provide a reading on the oil level in the oil reservoir to a user. Optionally, the dipstick further comprises a loop, a dipstick stop below the loop, a low reading below the dipstick stop and the method further comprises, before step d), laying the strip next to the dipstick so that the low reading is aligned with the at least one indicia and then moving the ratchet forwardly so that the ratchet is aligned with the dipstick stop. Optionally, the at least one indicia is in the form of a dimple. Optionally, the strip comprises a front surface and a rear surface, and further wherein the plurality of teeth are located on the front surface. Optionally, the tube is attached to the strip by a fastener at a fixed location along the strip length. Optionally, the strip bottom end is tapered. Optionally, oil in the oil reservoir is configured to absorb to the tube independent of the oil temperature. Optionally, the tube is flattened. Optionally, the tube is located above the strip bottom end. Optionally, the user places his fingers inside the loop during steps d) and step e).

In still further embodiments, the present disclosure provides: An oil level visualization system comprising: a strip comprised of a heat-resistant, non-oil absorbent material and having a top end comprising a loop, a bottom end, a length extending from the top end to the bottom end, a width perpendicular to the length, and a thickness perpendicular to the width and the length, wherein a tube located below the loop is attached to the strip, the tube comprised of an oil absorbent material and comprising a hollow interior receiving the strip, and further wherein the strip is the form of a cable tie comprising a plurality of teeth spaced along the length of the strip and a ratchet configured to engage the plurality of teeth, the ratchet forming a bottom end of the loop and located above the tube. Optionally, the oil absorbent material is a cellulosic material (e.g., a paper-based material). Optionally, the tube comprises at least one indicia visible to the naked eye. Optionally, tube is attached to the strip at a fixed location along the strip length. Optionally, the strip bottom end is tapered. Optionally, the loop comprises an adjustable size and further wherein moving the ratchet upwardly reduces the size of the loop and increases the length of the strip.

BRIEF DESCRIPTION OF THE DRAWINGS

FIG. 13 includes three indicia lines.

DETAILED DESCRIPTION

Figure 1:
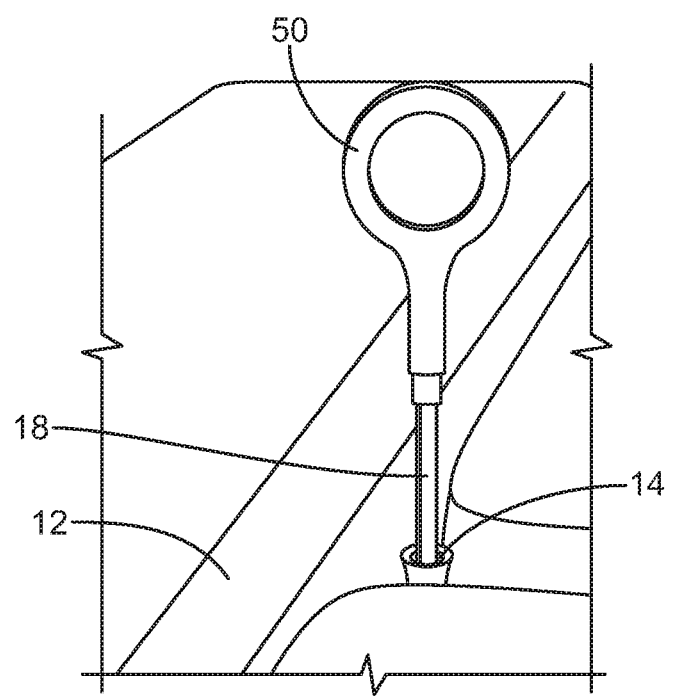
FIG. 1 illustrates a side, perspective view of a prior art dipstick, engine and oil reservoir.
Figure 2:
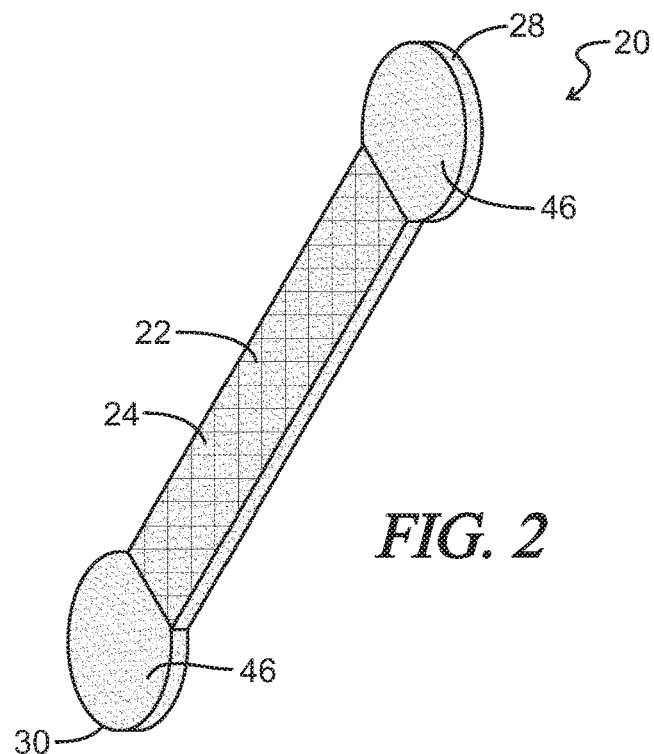
FIG. 2 illustrates a front, perspective view of a strip of one embodiment of the present invention.
Figure 3:
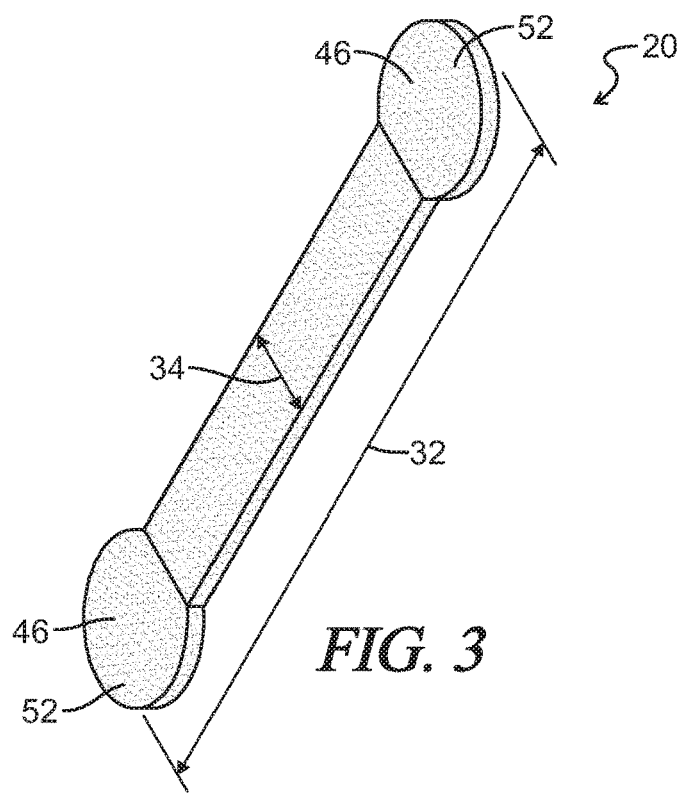
FIG. 3 illustrates a rear, perspective view of the strip of FIG. 2.
Figure 4:
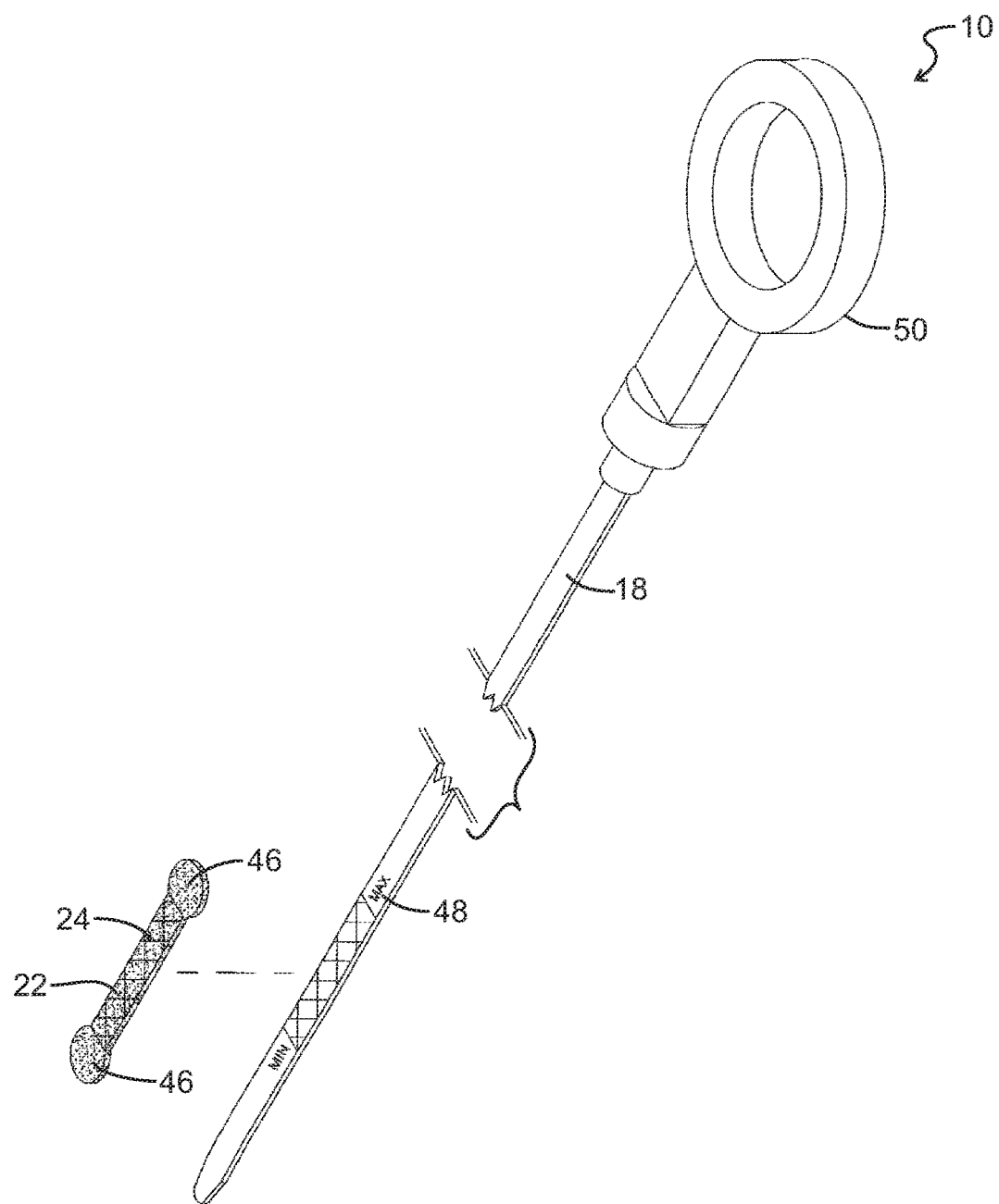
FIG. 4 illustrates an exploded, front, perspective view of a dipstick visualization system of one embodiment of the present invention.
Figure 5:
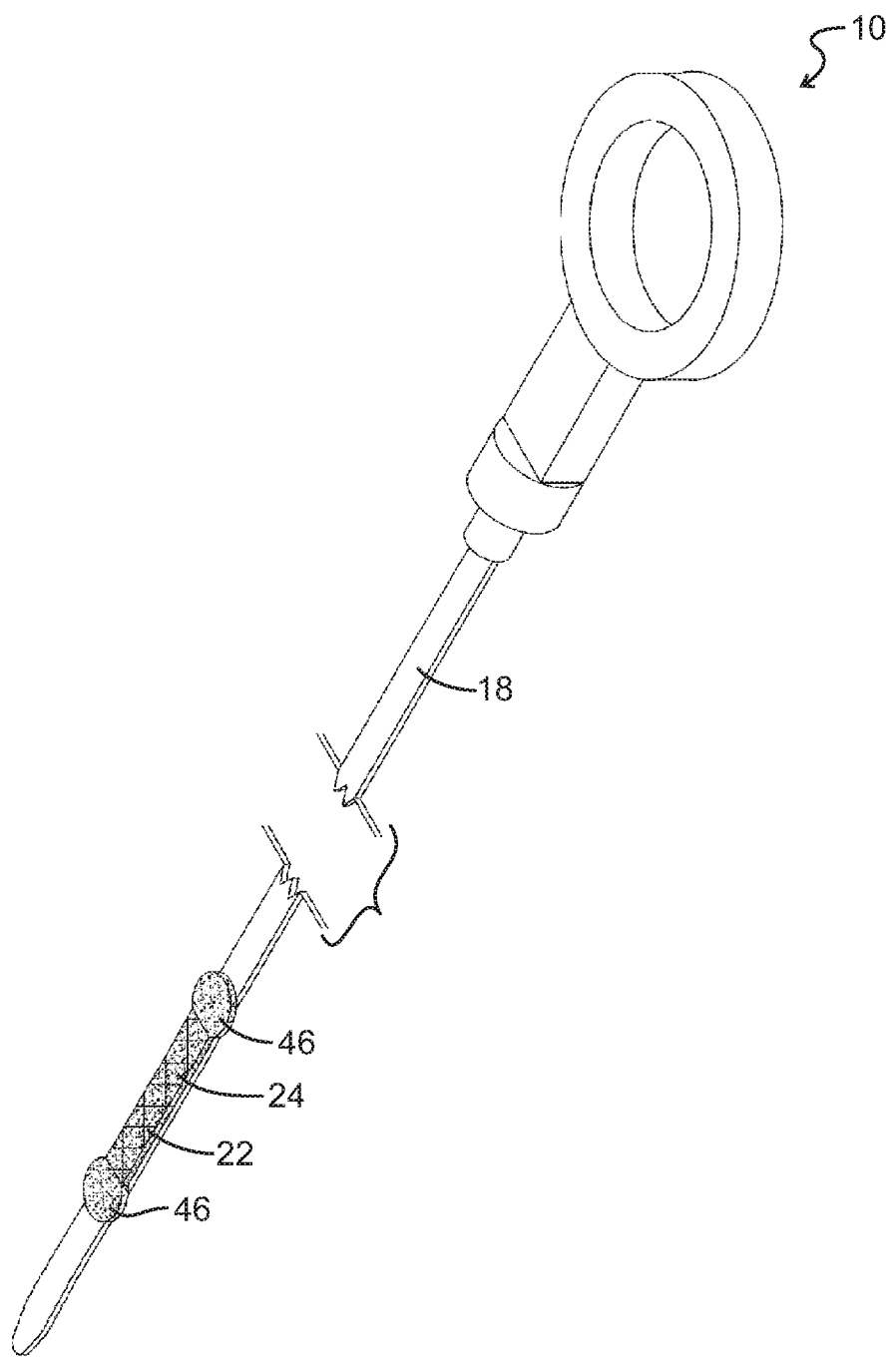
FIG. 5 illustrates an assembled, front, perspective view of the dipstick visualization system of FIG. 4.

With reference to FIGS. 1-9, the present invention provides a dipstick visualization system designated by the numeral 10. In the drawings, not all reference numbers are included in each drawing for the sake of clarity.

Figure 6:
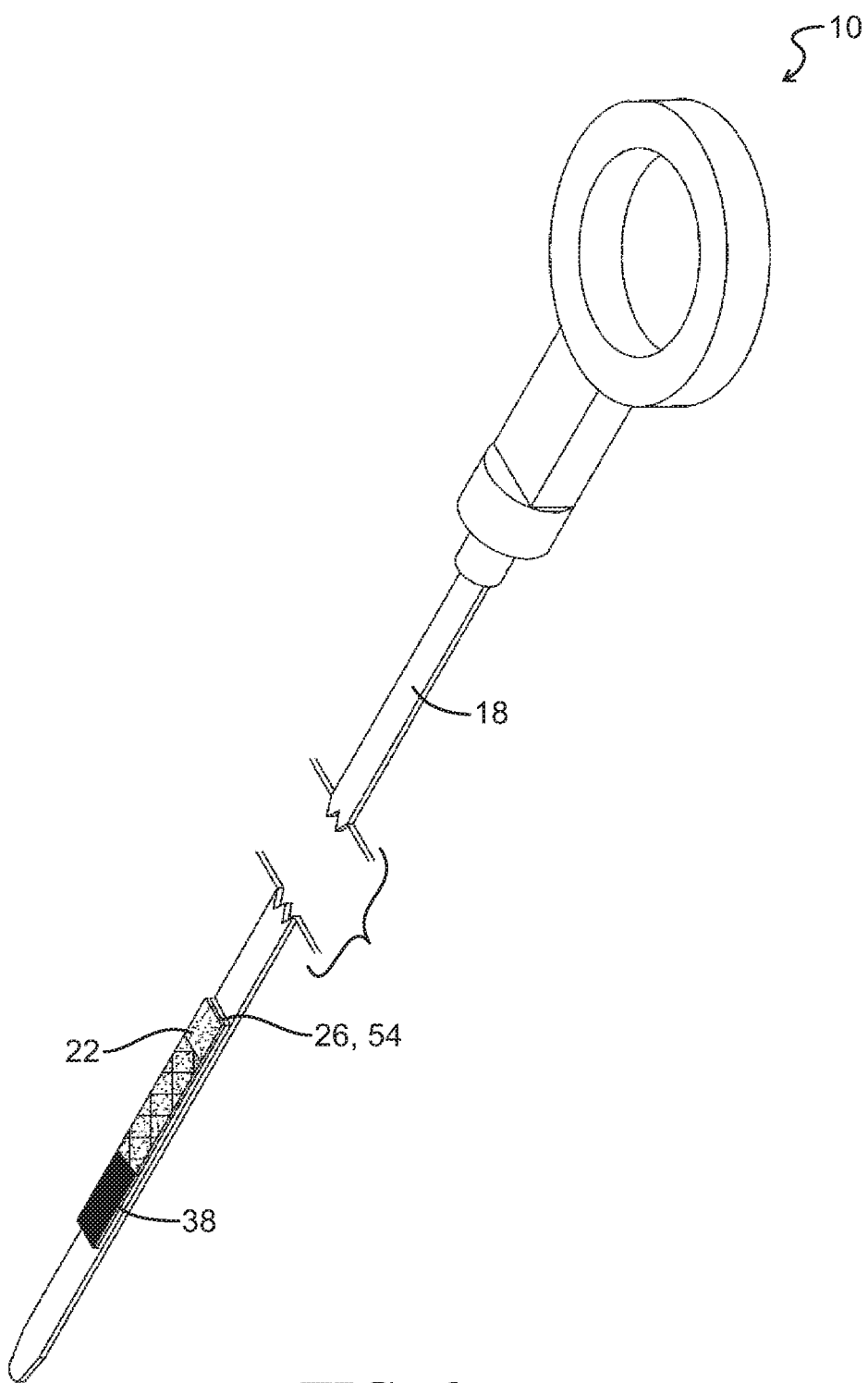
FIG. 6 illustrates an assembled, front, perspective view of a dipstick visualization system of another embodiment of the present invention; the system of FIG. 6 uses magnets on the strip rear surface to attach the strip to a metal dipstick; an oil stain is shown on FIG. 6.
Figure 7:
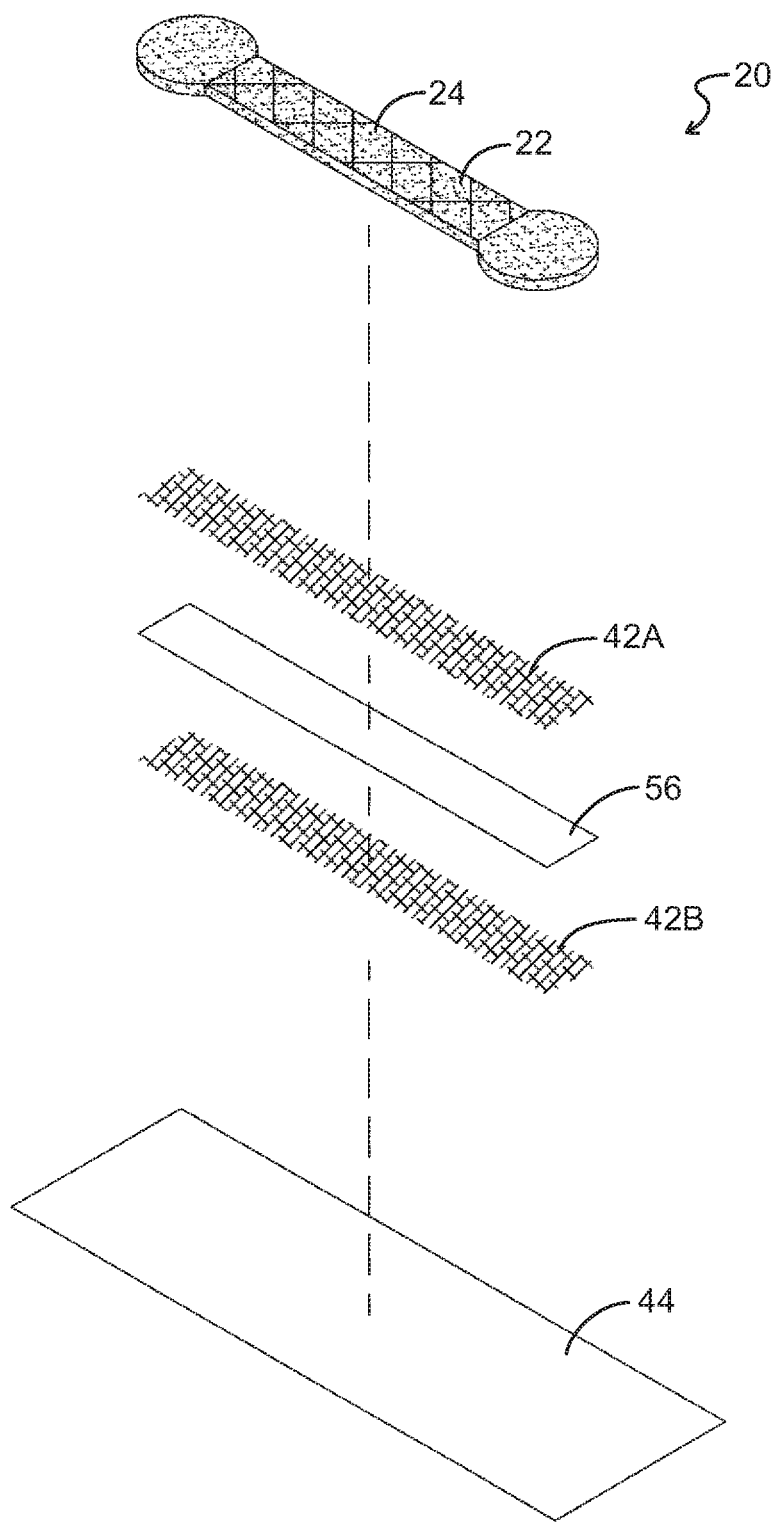
FIG. 7 illustrates a top, perspective view of a strip that includes multiple layers.
Figure 8A:
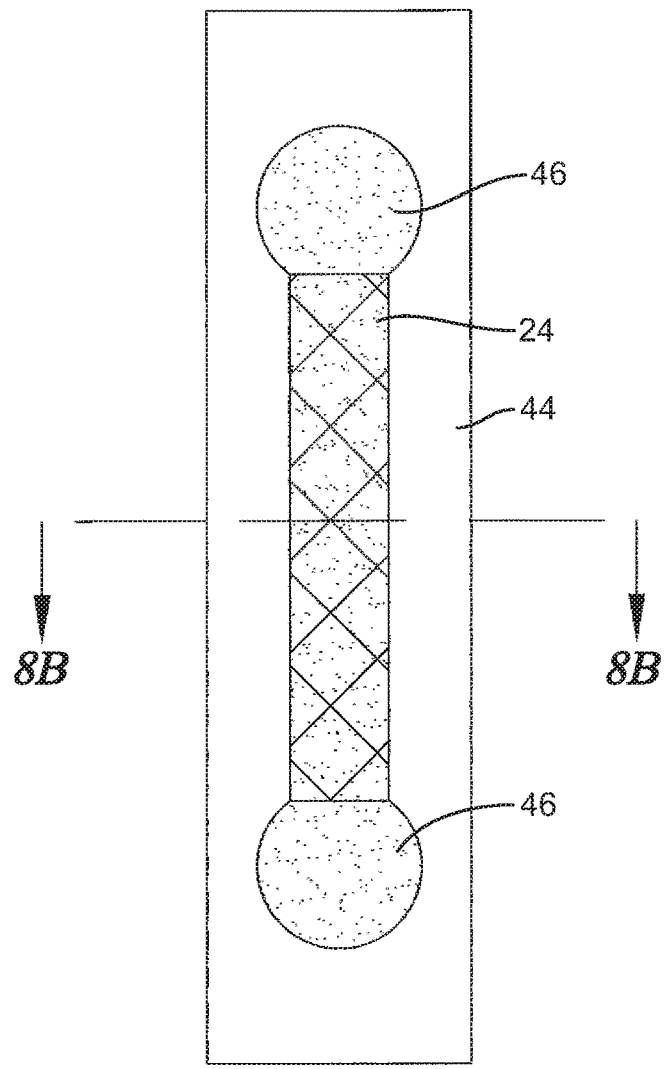
FIG. 8A illustrates a top, plan view of the strip of FIG. 7.
Figure 8B:
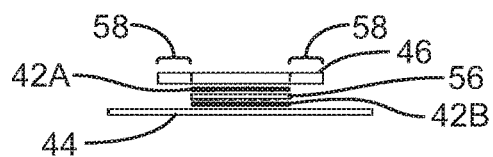
FIG. 8B illustrates a side cross-sectional view of the strip of FIG. 8A line A-A of FIG. 8A.
Figure 9:
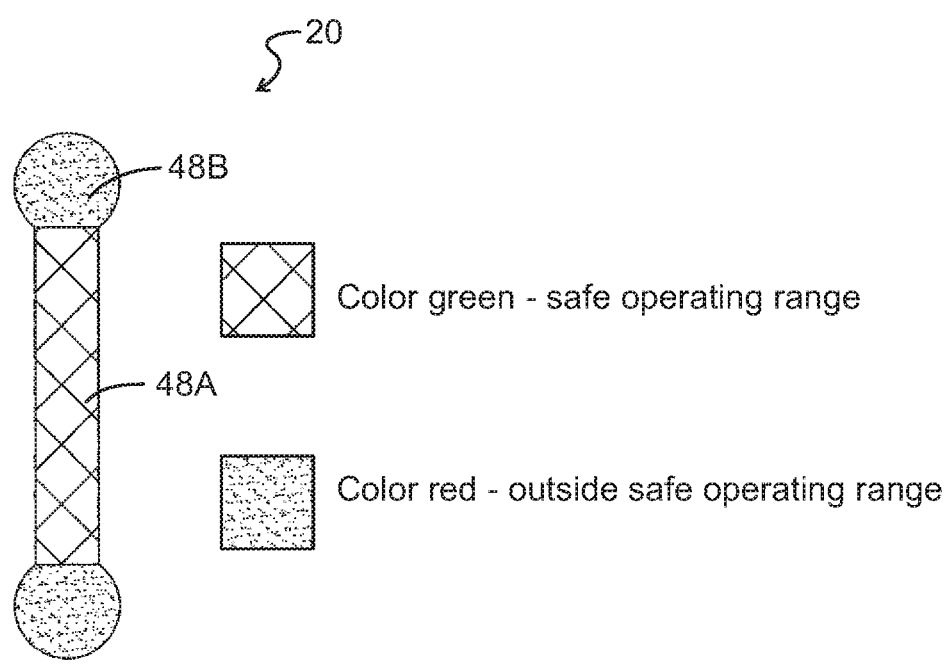
FIG. 9 illustrates a front, elevation view in which the strip front surface includes indicia configured to convey target oil level to the operator.

Referring further to FIGS. 1-9, in some embodiments, the system 10 includes: a) an engine 12 comprising an oil reservoir 14 configured to hold oil; b) a dipstick 18 configured to be disposed in the oil reservoir 14 and measure oil level in the oil reservoir 14; c) a strip 20 comprising a front surface 22 comprising an oil absorbent material 24 and a rear surface 26 configured to confront the dipstick 18; and d) a fastener 40 configured to removably attach the oil absorbent material 24 to the dipstick 18. (FIG. 1 is labelled prior art to reflect that engine oil dipsticks 18 without the strip are known in the art). Optionally, the dipstick 18 has a handle 50. Oil from the oil reservoir 14 is configured to absorb to the oil absorbent material 24 and absorbing of the oil to the oil absorbent material 24 is configured to provide a stain on the oil absorbent material 24 visible to the naked eye. Optionally, the fastener 40 is an adhesive sticker, a clip, or a magnet. For example, as shown in FIG. 7, the strip front surface 22 may be bounded to a plastic backing 56 by a first adhesive 42A and the plastic backing 56 may be bounded to a removable paper or paper-based backing 44 by a second adhesive 42B. The removable paper or paper-based backing 44 is configured to cover the second adhesive 42B until the strip 20 is used—i.e., the user removes the backing 44 to expose the adhesive 42B and the adhesive 42B is placed on the dipstick 18, thereby attaching the strip 20 to the dipstick 18. Alternatively, as shown in FIG. 6, the strip front surface 22 may be bounded to a magnet 54 and the magnet 54 removably attaches to the dipstick 18.

Optionally, the strip 20 comprises a top end 28, a bottom end 30, a length 32 extending from the top end 28 to the bottom end 30, pull tab(s) 46 located at the end(s) 28 and/or 30 of the strip 20, the pull tab(s) 46 having a rear surface 52 designed to confront the dipstick 18. The pull tab rear surface 52 is wider than the remainder of the strip 20.

Preferably, the adhesive 42 is located on the pull tab rear surface 52 at all locations except where the pull tabs 46 extend beyond the width of the remainder of the strip 20 (see numeral 58 in FIG. 8B) so that the tabs 46 do not roll up in the dipstick tube. (The dipstick tube is described later herein). Optionally, the oil absorbent material 24 is comprised of a cellulosic material, such as paper or paper-based material, e.g., paperboard or paper cardstock, and the oil absorbent material 24 forms all or substantially all of the front surface 22 of the strip 20. Optionally, the oil absorbent material 24 is comprised of cloth or felt. Optionally, the strip front surface 22 is comprised of a paper-based material and a plastic is behind the paper-based material (i.e., the strip rear surface 26 is comprised of plastic or, as shown in FIG. 7, there is an intermediate plastic layer 56 between the front and rear surfaces 22 and 26). Optionally, the strip rear surface 26 is comprised of brass and the strip front surface 22 is comprised of a paper-based material. Preferably, oil in the oil reservoir 14 is configured to absorb to the oil absorbent material 24 at ambient temperature and absorbing of the oil to the oil absorbent material 24 is configured to provide a stain 38 visible to the naked eye at ambient temperature. Preferably, oil in the oil reservoir 14 is configured to absorb to the oil absorbent material 24 independent of the oil temperature and absorbing of the oil to the oil absorbent material 24 is configured to provide a stain 38 visible to the naked eye, as shown in FIG. 6. Optionally, the strip length 32 (including tabs 46) is from about 1 inch to about 1.75 inches and the strip width 34 (including tabs 46), which is perpendicular to the length 32, is from about 3/16 inches (0.1875 inches) to about 0.3125 inches. In some embodiments, the tabs 46 have a combined length of about 0.25 inches to about 0.75 inches and each tab 46 has a width of about 0.25 inches to about 0.3125 inches.

Optionally, the strip width 34 is wider at the top end 28 and at the bottom end 30. As known to those of ordinary skill, a dipstick tube is the metal tube or sheath that the dipstick 18 slides into in the oil reservoir 14. These tubes are notorious for accumulating oil film that collects on the edges of a conventional flat dipstick 18 when it is removed from the oil reservoir 14; giving false readings. The wider ends 28 and 30 of the strip 20 (shown as tabs 46 in the drawing) swab oil film in the dipstick tube when the dipstick 18 is re-inserted into the reservoir 14, which the inventor believes will help to ensure accurate oil absorbent reading. Preferably, the oil absorbent material 24 extends to the tabs 46.

The strip rear surface 26 (including tabs 46) is preferably generally flat. Optionally, the strip 20 comprises at least one indicia, such as two colors (e.g., red 48B and green 48A) or a line to indicate a target oil level. The dipstick may also include indicia 48. Optionally, the dipstick 18 is comprised of metal.

Preferably, the system is used in a method that includes the following steps:

a) providing an engine 12 comprising an oil reservoir 14 configured to hold oil;

b) providing a dipstick 18 configured to be disposed in the oil reservoir 14 and measure oil level in the oil reservoir 14;

c) providing an oil absorbent material 24 comprising a rear surface 26 configured to confront the dipstick 18;

d) providing a fastener 40 configured to removably attach the oil absorbent material 24 to the dipstick 18;

e) using the fastener 40 to removably attach the oil absorbent material 24 to the dipstick 18;

f) placing (i.e., inserting) the dipstick 18 with the oil absorbent material 24 into the oil reservoir 14; and g) absorbing oil from the oil reservoir 14 to the oil absorbent material 24 to provide a stain on the oil absorbent material 24 visible to the naked eye.

Optionally, the oil absorbent material 24 is located on a strip 20 that attaches to the dipstick 18 as described above. Optionally, the method further includes: h) removing the oil absorbent material 24 from the dipstick 18—i.e., the strip 20 is designed for a single reading and is disposable.

As a general rule, the dipstick 18 (without the oil absorbent material 24) is typically located in the oil reservoir 14 in step A, the dipstick 18 is then removed from the oil reservoir 14 and preferably wiped before attaching the oil absorbent material 24 to the dipstick 18, and then the dipstick 18 with the oil absorbent material 24 is placed into the oil reservoir 14 as called for in step f.

The Embodiments of FIGS. 10-13

FIGS. 10-13 illustrate alternate embodiments of the invention in which a strip 60 is used in place of the user's dipstick 18. Referring to FIGS. 10-13, in the alternate embodiments, the strip 60 comprises an oil absorbent material 62, the strip 60 has a top end 64, a bottom end 66, a length 68 extending from the top end 64 to the bottom end 66, the length 68 being from about 4 inches to about 35 inches (more preferably from about 20 inches to about 35 inches), a width 70 perpendicular to the length 68, the width 70 being from about 0.15 inches to about 0.5 inches and a thickness 72 perpendicular to the length 68 and width 70, the thickness 72 being from about 0.015 inches to about 0.3 inches. Preferably, the thickness is from about 0.015 inches to about 0.05 inches. The strip 60 further includes a backing 61 that is comprised of a material different than the oil absorbent material 62. For example, in some embodiments, the backing 61 is metallic, such as aluminum, brass, copper, or tin foil or sheet that may be, for example, about 0.005 inches to about 0.015 inches thick. In other embodiments, the backing 61 is plastic, for example, that may be about 0.030 inches to about 0.125 inches thick. It will be understood that the thickness of the backing 61 is parallel to the thickness 72 of the strip 60. It will also be appreciated that the thickness of the backing 61 and the thickness of the oil absorbent material 62 is approximately equal to the thickness 72 of the strip 60, given that the thickness of the fastener 63 is generally negligible. It will also be appreciated that the thickness 72 of the strip 60 extends from the surface of the oil absorbent material 62 that is not in contact with the fastener 63 (i.e., the front of the strip 62) to the surface of the backing 61 that is not in contact with the fastener 63 (i.e., the rear of the strip 62). Preferably, the oil absorbent material 62 has a uniform thickness from the top end 64 to the bottom end 66 and the backing 61 also has a uniform thickness from the top end 64 to the bottom end 66. Typically, the thickness of the oil absorbent material 62 is greater than the thickness of the backing 61, as shown in FIGS. 10-13 and the oil absorbent material 62 and the backing 61 have the same width and length, as shown in FIGS. 10-13—i.e., the width of the oil absorbent material 62 and the width of the backing 61 are within 0.5 inches of each other and the length of the oil absorbent material 62 and the length of the backing 61 are within 0.5 inches of each other—it will be understood that the length of the oil absorbent material 62 and the length of the backing 61 are parallel to the length 68 of the strip 60 and the width of the oil absorbent material 62 and the width of the backing 61 are parallel to the width 70 of the strip 60. Optionally, a fastener 63 such as double-sided adhesive attaches the oil absorbent material 62 to the backing 61 and is located between the oil absorbent material 62 and the backing 61.

The strip 60 of FIGS. 10-13 is configured to act as a replacement dipstick and, unlike the prior embodiments, does not attach to the user's dipstick 18. It will be appreciated that the strip 60 of FIGS. 10-13 is also longer than the strips 20 of the prior embodiments.

Figure 10:
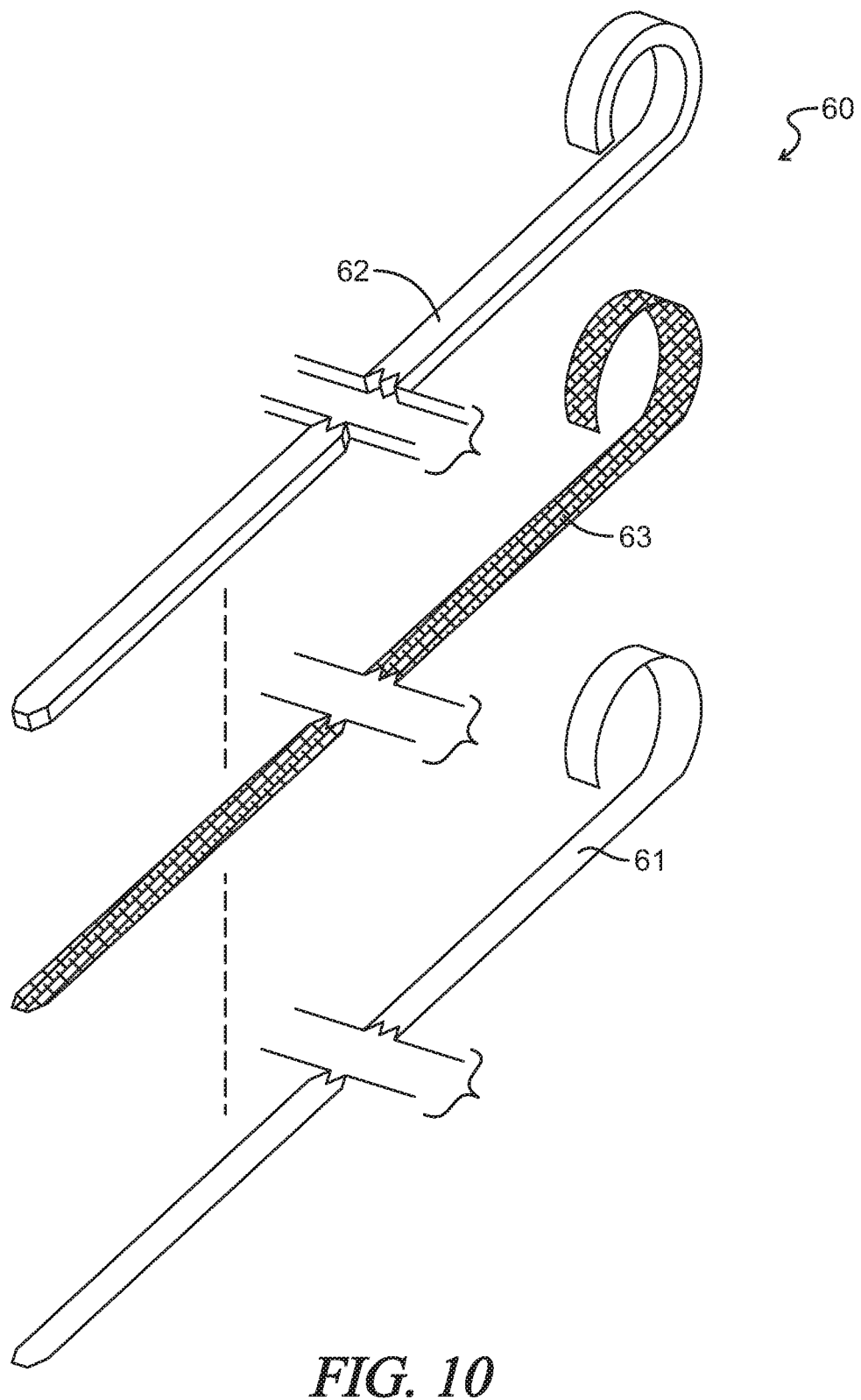
FIG. 10 illustrates a front, perspective, exploded view of a strip of an alternate embodiment of the present invention in which the strip includes an oil absorbent material, an adhesive and a backing; the top end of the strip is rolled to form a circular handle.
Figure 11:
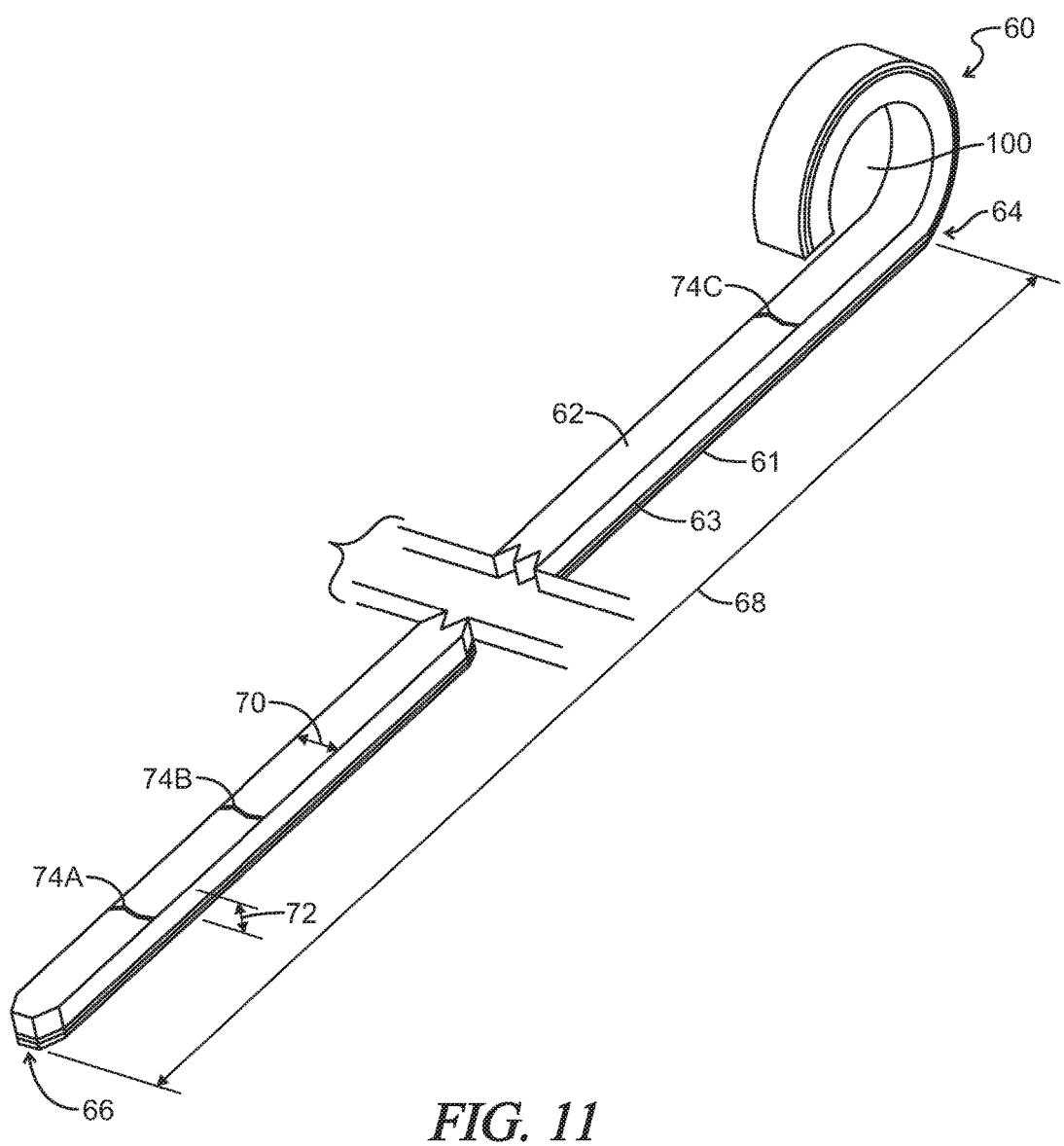
FIG. 11 illustrates a front, perspective, assembled view of the strip of FIG. 10 with three indicia lines on the oil absorbent material.
Figure 12:
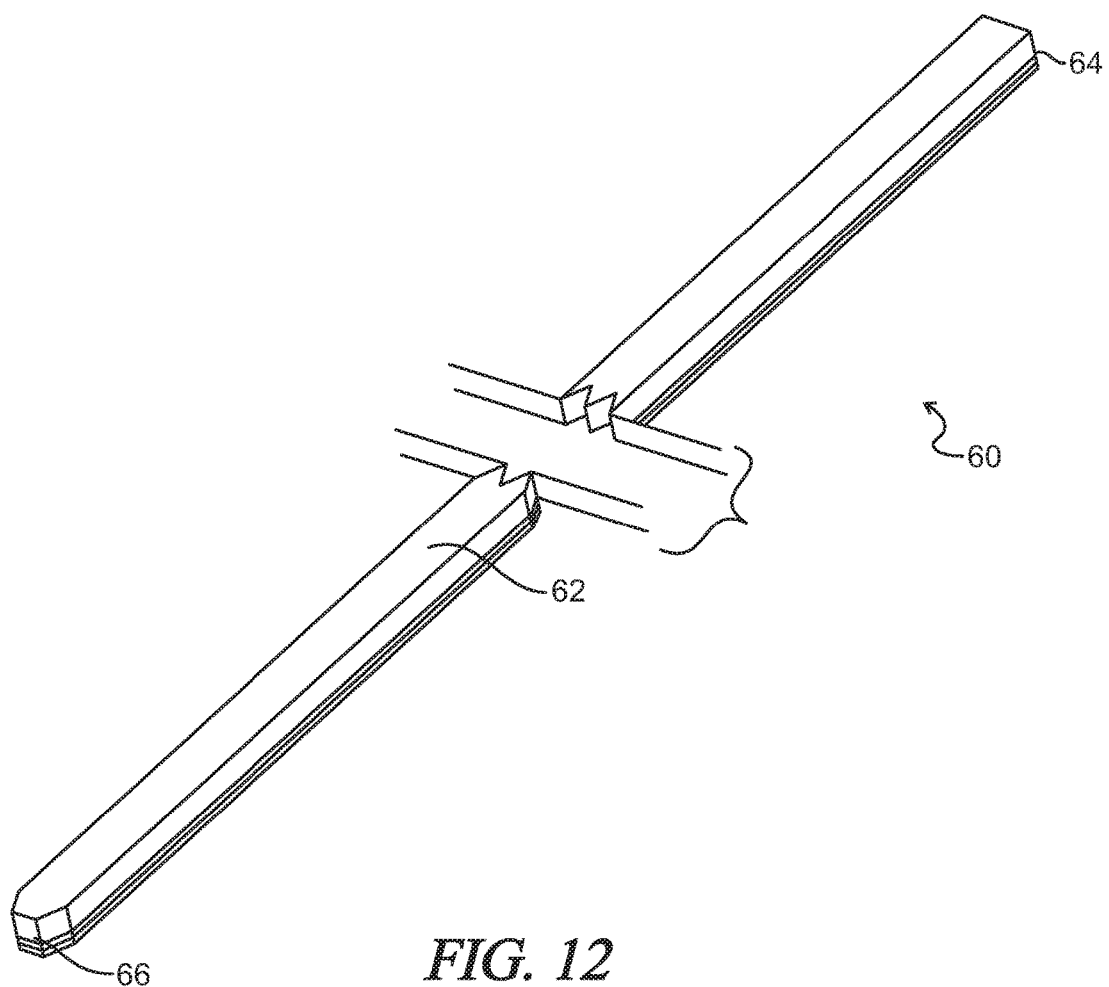
FIG. 12 illustrates a front, perspective view of an alternate embodiment of a strip that includes an oil absorbent material, an adhesive and a backing; the strip is straight.
Figure 13:
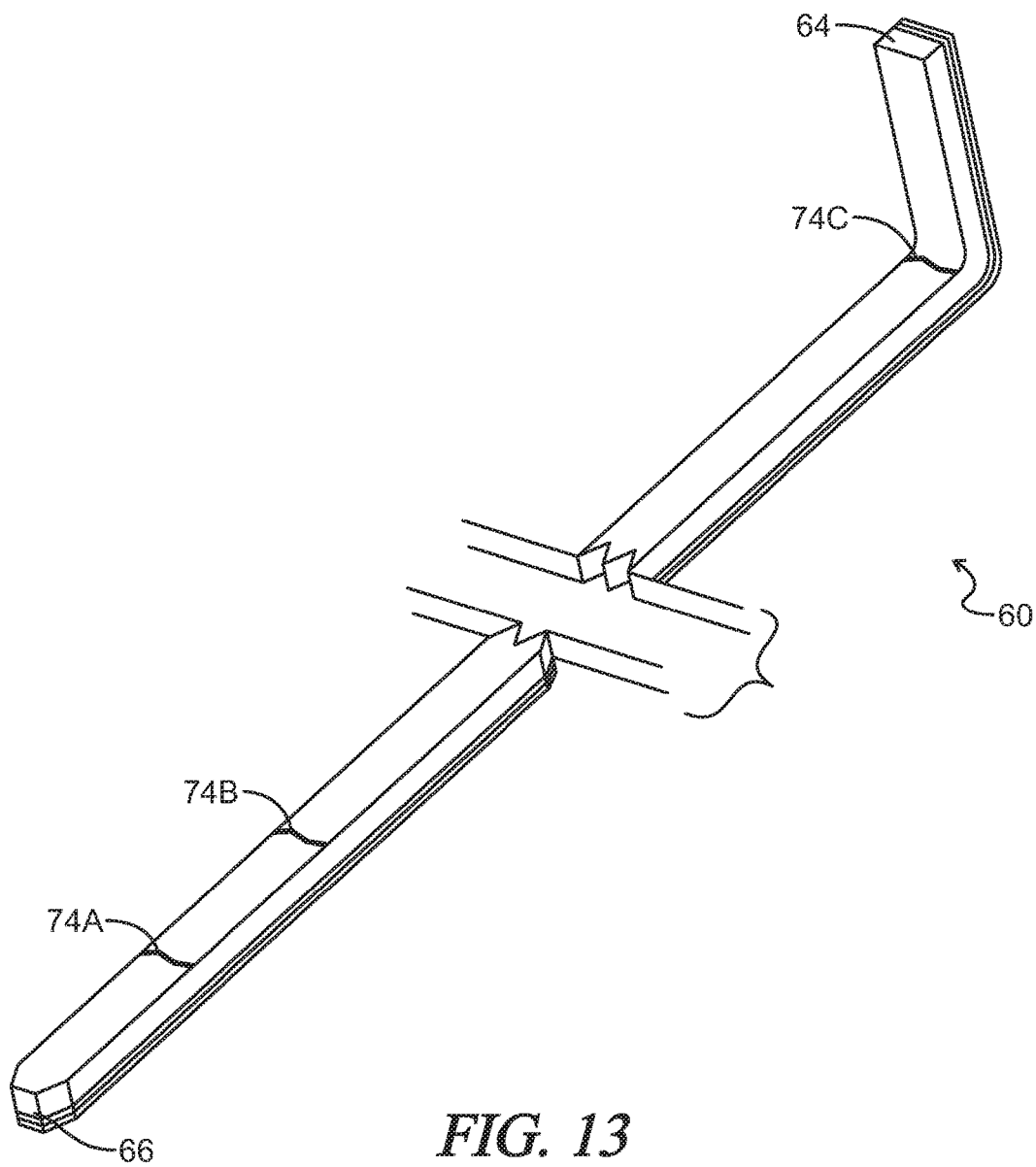
FIG. 13 illustrates a front, perspective view of the strip of FIG. 12 in which the top end of the strip has been bent by a user.

Optionally, as shown in FIGS. 10-13, the strip 60 has generally a uniform width 70 except for the bottom end 66, which may be tapered as shown in FIGS. 10-13. The top end 64 may roll onto itself to form a generally circular handle 100, as shown in FIGS. 10-11. In other embodiments, as shown in FIG. 12, the strip 60 may be provided generally straight from the manufacturer and then the user may bend the top end 64 approximately 90 degrees relative to the bottom end 66 as shown in FIG. 13.

The strip 60 may be made through any suitable process. In one exemplary process, four to eight foot long sheets of 30 inch wide paper board (i.e., the oil absorbent material 62), double-sided adhesive (i.e., the fastener 63), and backing 61 are pressed together on a specialized machine to form a large laminated sheet. Subsequently, the lamination machine or a separate piece of equipment horizontally shears or rotary slits the 30 inch wide sheet into 3/16 inch wide by 30 inch long strips 60. A secondary operation punches the tapered bottom end 66. It will be understood that the aforementioned method is only exemplary.

The user may be supplied with a package containing a plurality of strips 60 or alternately, the user may be provided with a package containing a roll and the user may cut the roll with a sharp blade like a piece of tape to form each individual strip 60 for use.

The oil absorbent material 62 is preferably non-metallic. For example, the oil absorbent material 62 may be comprised of a cellulosic material, preferably a rigid material such as paper cardstock or paper board.

Optionally, as with the prior embodiments, oil in the oil reservoir 14 is configured to absorb to the oil absorbent material 62 at ambient temperature and absorbing of the oil to the oil absorbent material 62 is configured to provide a stain visible to the naked eye at ambient temperature. Optionally, as with the prior embodiments, oil in the oil reservoir 14 is configured to absorb to the oil absorbent material 62 independent of the oil temperature and absorbing of the oil to the oil absorbent material 62 is configured to provide a stain visible to the naked eye. Optionally, the oil absorbent material 62 comprises at least one indicia, such as two colors (e.g., red and green) or a line(s) to indicate a target oil level.

Optionally, the strip 60 of FIGS. 10-13 is used in a method that includes:

a) providing an engine comprising an oil reservoir 14 configured to hold oil, the oil reservoir 14 comprising a dipstick 18 configured to measure oil level in the oil reservoir 14;

b) removing the dipstick 18 from the oil reservoir 14;

c) providing the strip 60 and inserting the strip 60 into the oil reservoir 14;

d) absorbing oil from the oil reservoir 14 to the oil absorbent material 62 to provide a stain on the oil absorbent material 62 visible to the naked eye; and e) removing the strip 60 from the oil reservoir 14 and reading the oil level.

In the method described above, the strip 60 may be pre-marked from the manufacturer with the indicia. In an alternate embodiment and more typically, the user may lay his/her dipstick 18 next to the strip 60 and then draw at least one line on the oil absorbent material 62 prior to step d). For example, the user may draw three lines 74A-C across the width of the oil absorbent material 62 at the same location as the lines located on his/her conventional dipstick 18: a first line 74A for the minimum oil range, a second line 74B for the maximum oil range and a third line 74C for the contact point with the dipstick tube (so the strip 60 is inserted to proper depth). Optionally, the user bends the strip 60 near the top line 74C as shown in FIG. 13. Optionally, prior to step d), the top end 64 of the strip 60 is bent by the user relative to the bottom end 66. In addition, generally the bottom end 66 of the strip 60 is the first part of the strip 60 that enters the oil reservoir 14.

It will be appreciated that the strips 20 and 60 described herein are preferably for temporary use—i.e., disposable after one use—and are generally not intended to be left in the oil reservoir 14 for an extended period of time. Thus, the strips 20 and 60 need not be configured to withstand corrosion when left in an oil reservoir 14.

The Embodiments of FIGS. 14-17

FIGS. 14-17 illustrate alternate embodiments of the invention in which a strip 100 is used in place of the user's conventional dipstick 18. With reference to FIGS. 14-17, the strip 100 includes an oil absorbent material 102 and has a top end 104, a bottom end 106, a length 108 extending from the top end 102 to the bottom end 104, a left side 110, a right side 112 and a width 114 extending from the left side 110 to the right side 112 and perpendicular to the length 108. As with the prior embodiments, the strip 100 is placed in the oil reservoir 14 after removing the conventional dipstick 18 and absorbing oil from the oil reservoir 14 to the oil absorbent material 102 is configured to provide a stain 124 on the oil absorbent material 102 visible to the naked eye. Optionally, the user draws indicia (e.g., a plurality of lines 122A-C) on the oil absorbent material 102 prior to inserting the strip 100 into the oil reservoir 14. Optionally, the user draws a plurality of lines 122A-C on the oil absorbent material 102 prior to inserting the strip 100 in the oil reservoir 14. For example, as with the prior embodiment, the user may draw a first line 122A for the minimum oil range, a second line 122B for the maximum oil range and a third line 122C for the contact point with the dipstick tube (so the strip 100 is inserted to proper depth). Optionally, the third line 122C is adjacent to the top end 104. Optionally, the first line 122A is adjacent to the bottom end 106.

Figure 15:
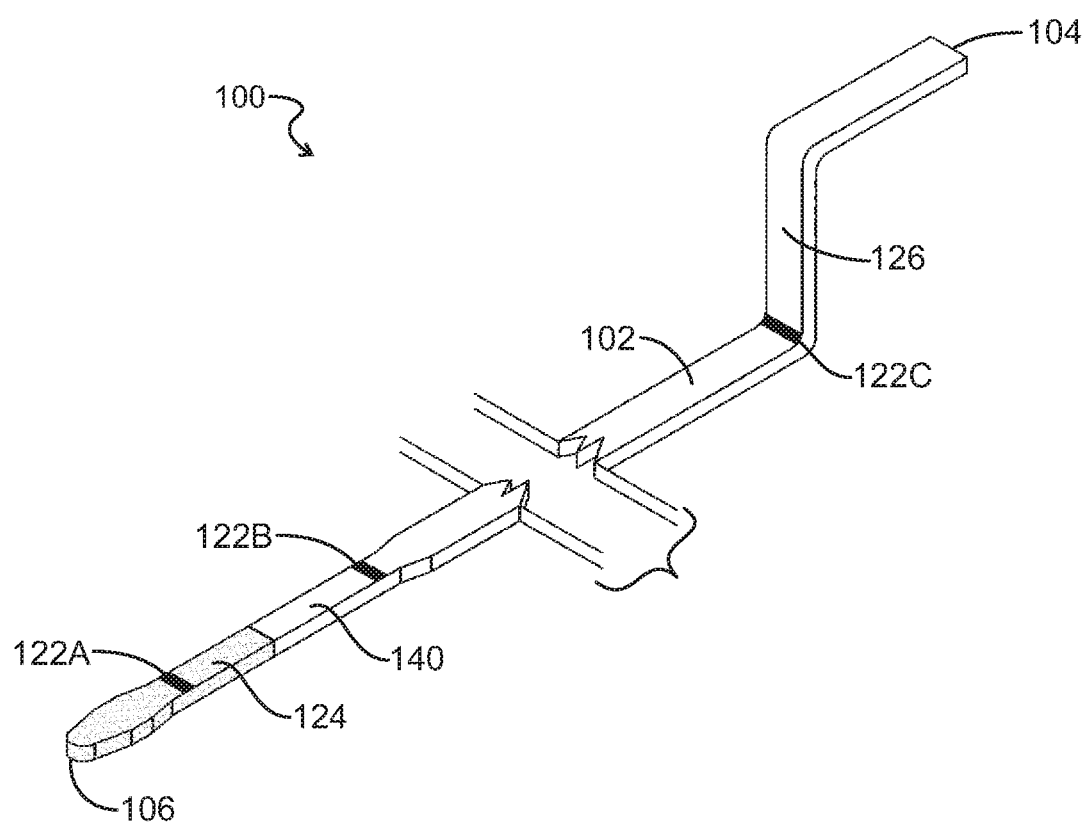
FIG. 15 illustrates a front, perspective view of the strip of FIG. 14 after the strip has been inserted in the oil reservoir.

The oil absorbent material 102 is preferably non-metallic. Optionally, the oil absorbent material 102 is comprised of a cellulosic material. Optionally, the oil absorbent material 102 is comprised of paper cardstock or paper board. In some embodiments, the strip 100 consists essentially of paper cardstock or paper board. For example, the strip 100 may consist only of paper cardstock or paper board when the strip 100 is placed in the oil reservoir 14 to provide an economical and easy-to-use solution. For example, in a particularly preferred embodiment, the strip 100 is made up entirely of recycled paper board, otherwise known as chipboard. Optionally, the strip 100 is capable of being bent by a user with his/her hands. Optionally, the user bends a segment 126 of the strip 100 relative to the bottom end 106 and the bent segment 126 is adjacent to (and between) the top end 104 and the third line 122C, as shown in FIG. 15. Optionally, after bending, the segment 106 is generally perpendicular to the remainder of the strip 100. Optionally, as with the prior embodiments, oil in the oil reservoir 14 is configured to absorb to the oil absorbent material 102 at ambient temperature and absorbing of the oil to the oil absorbent material 102 is configured to provide a stain 124 visible to the naked eye at ambient temperature. Optionally, oil in the oil reservoir 14 is configured to absorb to the oil absorbent material 102 independent of the oil temperature and absorbing of the oil to the oil absorbent material 102 is configured to provide a stain 124 visible to the naked eye. Optionally, the strip 100 comprises a front surface 116, a rear surface 118, a thickness 120 extending from the front surface 116 to the rear surface 118, the thickness 120 perpendicular to the strip length 108 and strip width 114 and further wherein the thickness 120 is from about 0.05 inches to about 0.3 inches, more preferably from about 0.0625 to about 0.1875 inches. The thickness 120 of the strip 100 is designed so that the strip 100 may include only the oil absorbent material 102 (e.g., paper cardstock or paper board) and the strip 100 is rigid yet bendable so that the strip 100 may be used in place of the conventional dipstick 18. For example, in a particularly preferred embodiment, the strip 100 is made up entirely of recycled paper board, otherwise known as chipboard. Optionally, the top end 104 of the strip 100 is rolled to create a generally circular handle, as with the prior embodiment. Optionally, the length 108 of the strip 100 is from about 4 inches to about 35 inches, more preferably from about 20 inches to about 35 inches.

Figure 14:
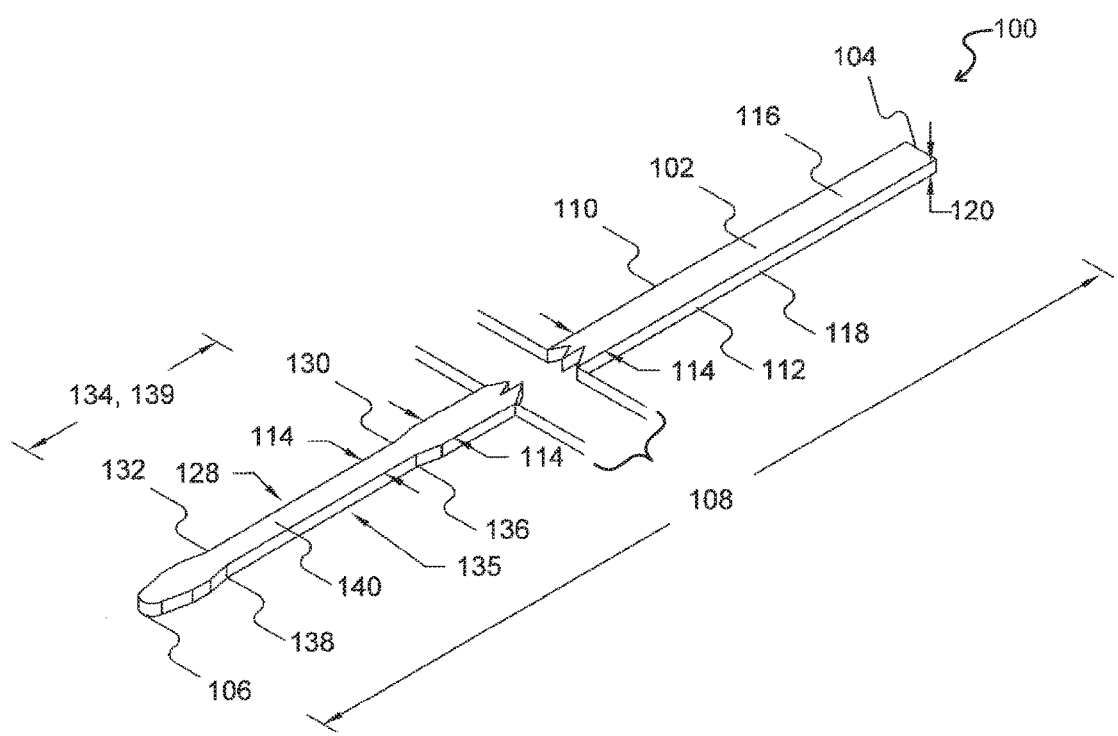
FIG. 14 illustrates a front, perspective view of a strip of another embodiment of the present invention prior to insertion in an oil reservoir.
Figure 16:
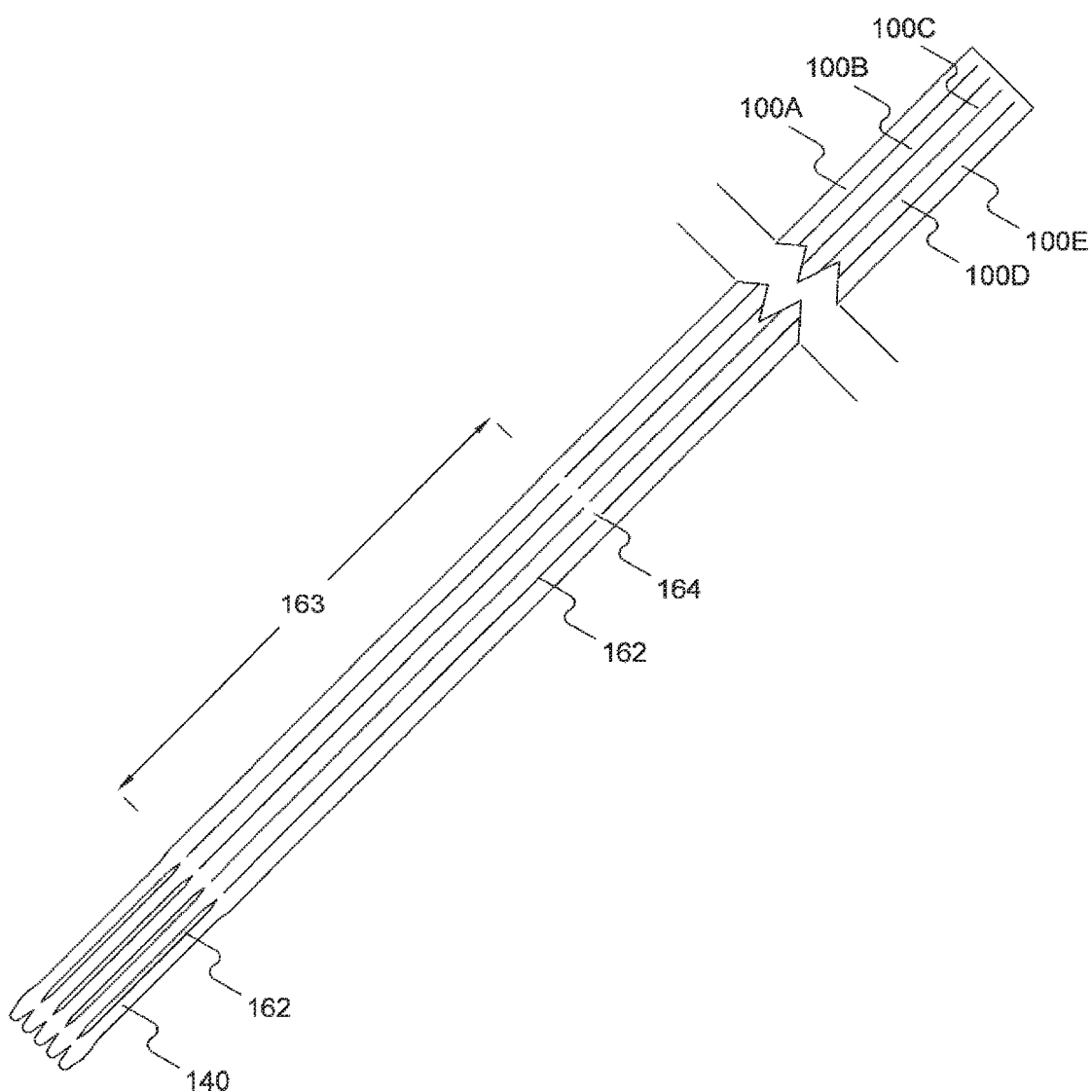
FIG. 16 illustrates a front, perspective view of connected strips of another embodiment of the present invention for use in a package.

In some embodiments, as shown in FIGS. 14-16, the strip 100 comprises a variable width 114 adjacent to the target oil level reading range. For example, the left side 110 of the strip 100 may include a left indentation 128 adjacent to the bottom end 106 of the strip 100 and the right side 112 of the strip 100 may include a right indentation 135 adjacent to the bottom end 106 of the strip 100. The left indentation 128 may include a left indentation top end 130, a left indentation bottom end 132, and a left indentation length 134 extending from the left indentation top end 130 to the left indentation bottom end 132. The right indentation 135 may include a right indentation top end 136, a right indentation bottom end 138, and a right indentation length 139 extending from the right indentation top end 136 to the right indentation bottom end 138. The left indentation top end 130, the left indentation bottom end 132, the right indentation top end 136 and the right indentation bottom end 138 define a tapered segment 140. Optionally, the distance from the left indentation top end 130 to the right indentation top end 136 (i.e., the strip width 114 in the tapered segment 140) is from about 0.05 to about 0.25 less than the strip width 114 directly above the left indentation top end 130 and the right indentation top end 136—meaning that the strip width 114 in the tapered segment 140 is from about 0.05 to about 0.25 less than the strip width 114 directly above the tapered segment 140. Optionally, the distance from the left indentation top end 130 to the right indentation top end 136 is between about 0.1 inches and about 0.2 inches and further wherein the width 114 of the strip 100 directly above the left indentation top end 130 and the right indentation top end 136 is from about 0.15 inches to about 0.35 inches. Similarly, optionally, the distance from the left indentation bottom end 132 to the right indentation bottom end 138 (i.e., the strip width 114 in the tapered segment 140) is from about 0.05 to about 0.25 less than the strip width 114 directly below the left indentation bottom end 132 and the right indentation bottom end 138. Optionally, the user draws two lines 122A and 122B on the oil absorbent material 102 in the tapered segment 140 prior to inserting the strip 100 into the oil reservoir 14. Optionally, after inserting the strip 100 in the oil reservoir 14, an oil stain 124 is located in the tapered segment 140, as shown in FIG. 15. As with the tabs 46, the larger width 114 immediately above and below the tapered segment 140 swab oil film in the dipstick tube when the strip 100 is inserted into and removed from the reservoir 14, which the inventor believes will help to ensure accurate oil absorbent reading. More particularly, oil film in the bore of the oil reservoir 14 dipstick tube is wiped by the larger width 114 immediately above and below the tapered segment 140 yielding more accurate oil level readings in tapered segment 140. Optionally, the left indentation 128 and the right indentation 135 are generally rectangular in shape.

Figure 17:
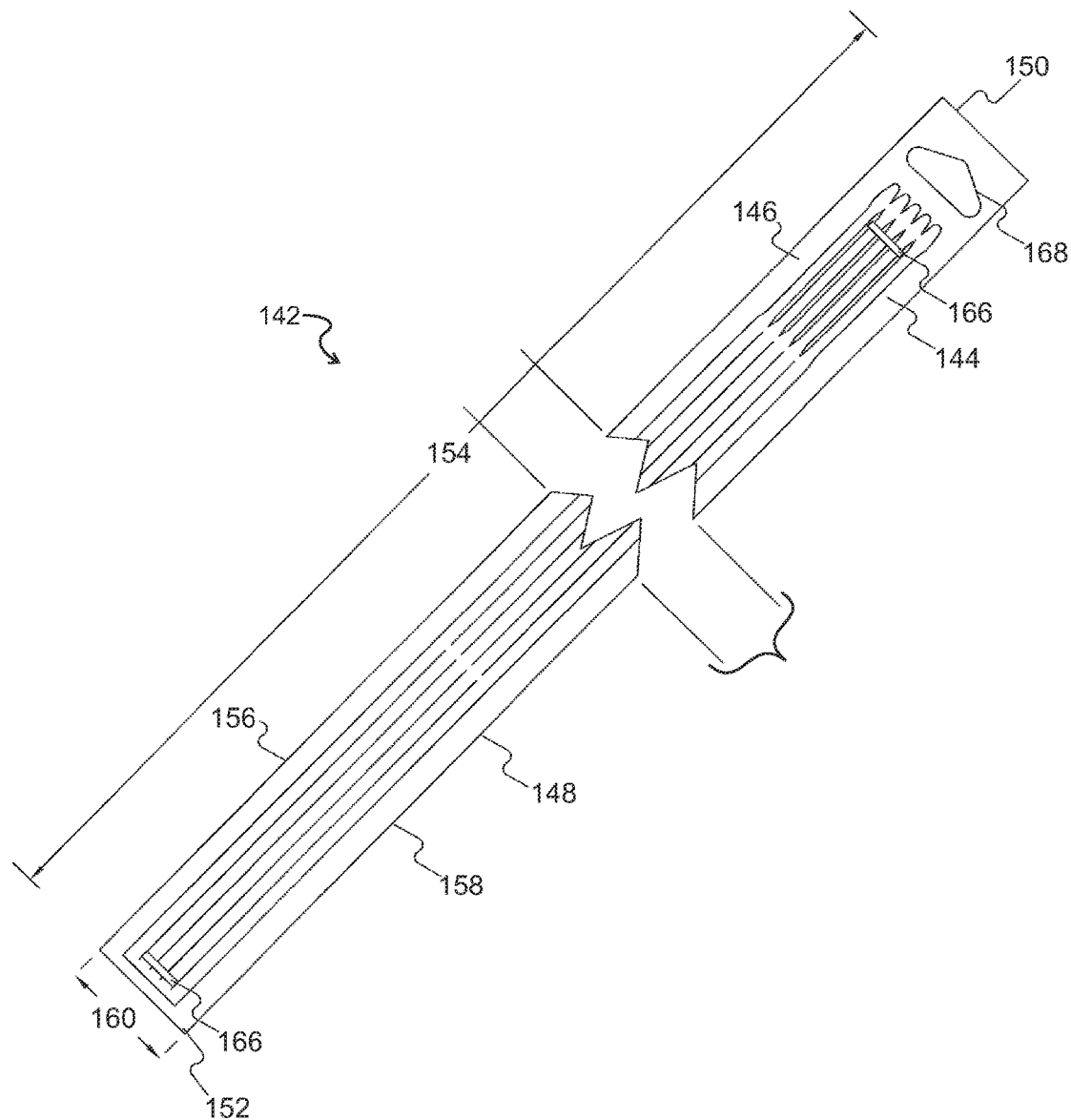
FIG. 17 illustrates a front, perspective view of a package of connected strips of another embodiment of the present invention.

Consumer retail packaging for the strip 100 will now be described. It will be understood that the description below is exemplary. Optionally, the consumer retail packaging is a package 142 that includes a plurality of strips 100A-E, as shown in FIG. 17. More particularly, the package 142 may include a package backing 144 comprising a package backing front surface 146, a package backing rear surface 148, a package backing top end 150, a package backing bottom end 152, a package backing length 154 extending from the package backing top end 150 to the package backing bottom end 152, a package backing left side 156, a package backing right side 158, and a package backing width 160 extending from the package backing left side 156 to the package packing right side 158. The package 142 may further include a plurality of adjacent strips 100A-E located on the package backing front surface 146, each of the plurality of adjacent strips 100A-E contacting the package backing front surface 146. As previously described, each of the plurality of adjacent strips 100A-E include an oil absorbent material 102, a top end 104, a bottom end 106, a length 108 extending from the top end 104 to the bottom end 106, a left side 110, a right side 112, and a width 114 extending from the left side 110 to the right side 112, the widths 114 of the plurality of adjacent strips 100A-E generally parallel to the package backing width 160 and the lengths 108 of the plurality of adjacent strips 100A-E generally parallel to the package backing length 154. In other words, strips 100A-E are located side-by-side, as shown in FIGS. 16-17. (FIG. 16 shows the strips 100A-E without the package backing 144). In an exemplary embodiment, the package backing 144 is cardboard. The strips 100A-E may be partially separated by a plurality of slots 162 located between adjacent sides 110 and 112 of adjacent strips 100A and 100B (for example), each slot 162 having a slot length 163 generally parallel to the strip length 108, the plurality of slots 162 located in front of the package backing front surface 146. The plurality of strips 100A-E may be connected by a plurality of bridges 164, each bridge 164 integral with the strips 100A-E connected by the bridge 164 and comprised of the same material as the strips 100A-E connected by the bridge 164, each bridge 164 interrupting a slot 162. The package backing 144 may be for example a continuous piece of cardboard. One or more fasteners 166 may connect the plurality of strips 100A-E to the package backing 144. Prior to using, the user separates a strip 100A from the other strips 100B-E and the package backing 144 (e.g., by cutting or tearing) and inserts the strip 100A separated from the other strips 100B-E and the package backing 144 into the oil reservoir 14. Optionally, the fastener 166 is a cord (e.g., a twist tie, e.g., a plastic tie), the cord passes through at least two of the slots 162 and through a fastener hole (not shown) in the package backing 144 (which extends from the package backing front surface 146 to the package backing rear surface 148) so that the cord may be tied on the package backing rear surface 148. Optionally, the user draws at least one line 122 on the oil absorbent material 102 of the plurality of adjacent strips 100A-E prior to removing a strip 100A from the backing 144 so that all strips 100A-E may be marked at once. The unused strips 100B-E are stored for later use. Optionally, the package backing length 154 is greater than the length 108 of each of the plurality of adjacent strips 100A-E and the package backing 144. Optionally, the package backing 144 includes a hanger hole 168 so that the package 142 may be hung on the wall of a retail store. The package 142 described above allows for an inexpensive way to make the strips 100A-E in that the strips 100A-E may be cut from a single piece of paper cardstock or paper board by a laser. Optionally, the plurality of strips 100A-E are covered with plastic to protect against moisture.

Figure 18:
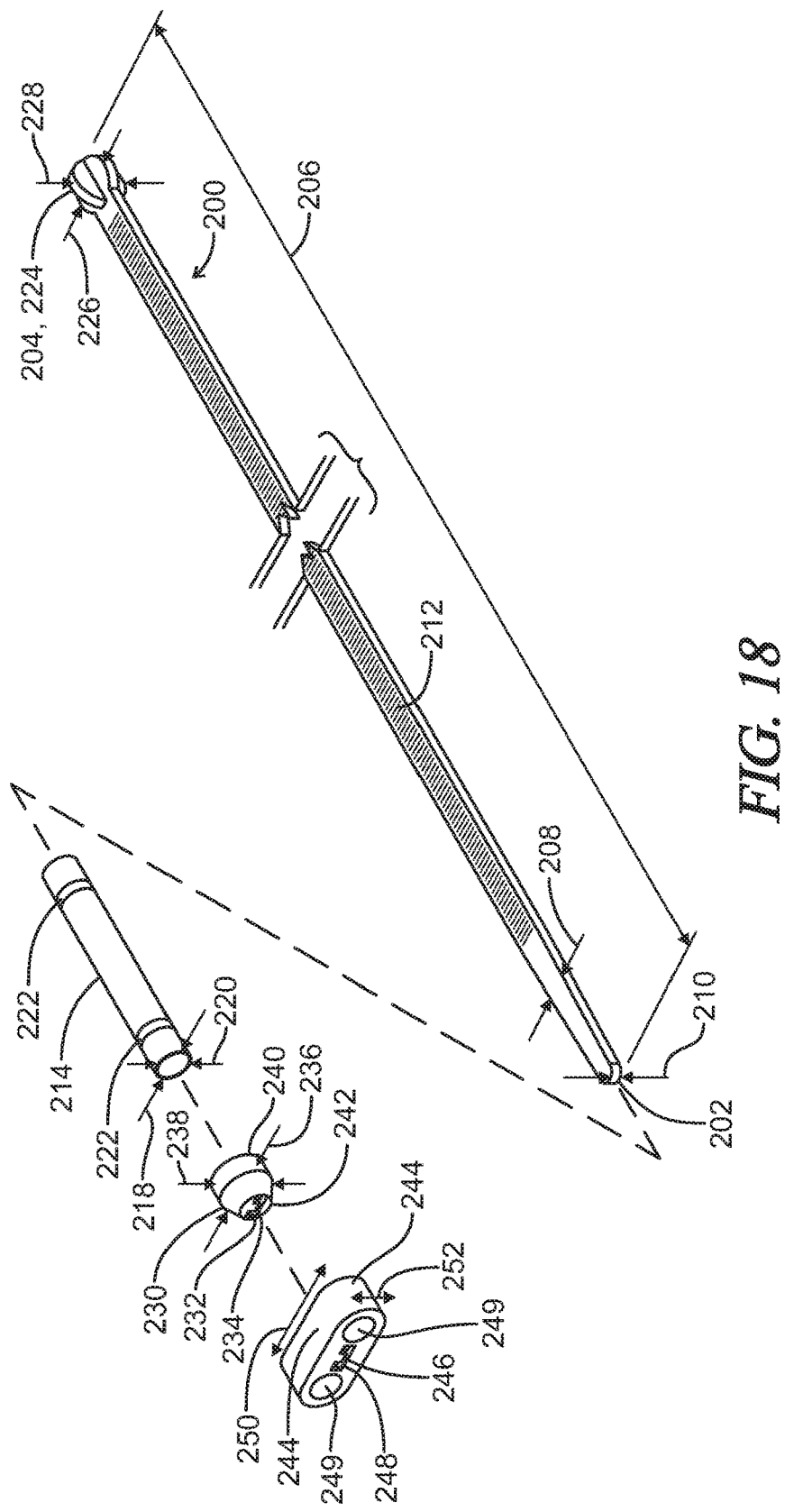
FIG. 18 illustrates a front, exploded perspective view of an oil level visualization system of another embodiment of the present invention.
Figure 19:
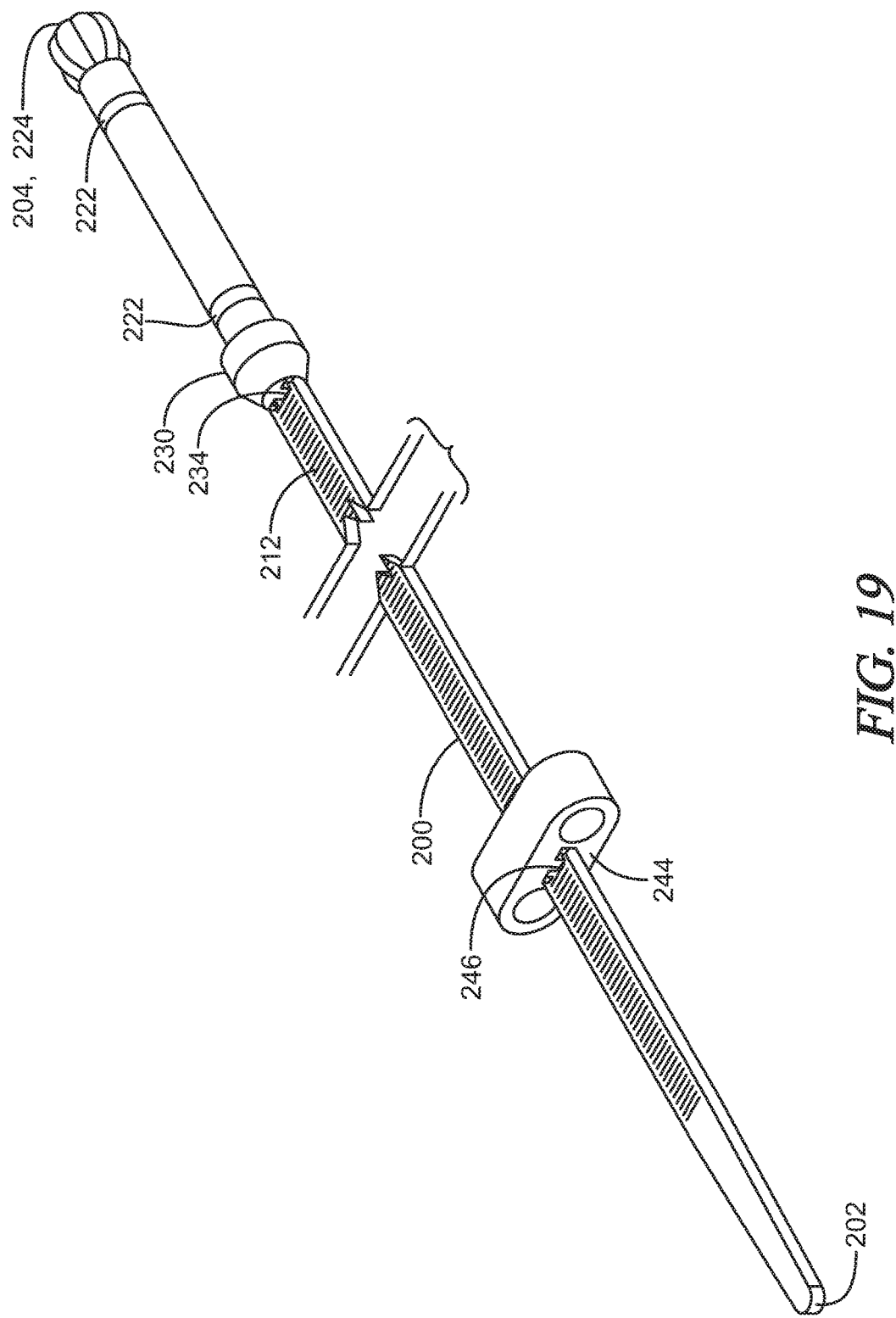
FIG. 19 illustrates a front, assembled perspective view of the oil level visualization system of FIG. 18.

The Embodiments of FIGS. 18-19

FIGS. 18-19 depict another embodiment of an oil level visualization system in which a strip is used instead of the user's dipstick. More particularly, like the previous embodiments, the system includes an engine 12 comprising an oil reservoir 14 configured to hold oil. As mentioned before, the oil reservoir 14 may include a dipstick tube. The strip 200 has a top end 202, a bottom end 204, a length 206 extending from the top end 202 to the bottom end 204, a width 208 perpendicular to the length 206, and a thickness 210 perpendicular to the width 208 and the length 206. The strip 200 is preferably comprised of a heat resistant non oil-absorbent material, such as plastic. The system further includes an oil absorbent material, such as a paper-based material. The oil absorbent material may be attached to the strip 200 using a fastener. For example, in one embodiment, the oil absorbent material is in the form of a tube 214, the tube 214 comprising a hollow interior 216 receiving the strip 200. The oil absorbent material forming the tube 214 may be positioned on (e.g., slid over) the strip 200 by the user or the manufacturer. At least the bottom end 204 of the strip 200 and the tube 214 are inserted into the oil reservoir 14 and oil from the oil reservoir 14 is absorbed to the tube 214 to provide a stain on the tube 214 visible to the naked eye.

Optionally, prior to inserting the tube 214 into the oil reservoir 14, the tube 214 comprises at least one indicia 222 visible to the naked eye, the indicia 222 configured to provide a reading on the oil level in the oil reservoir 14 to a user. As mentioned previously, a user may draw the indicia 222 on the oil absorbent material or the indicia 222 may be pre-labelled by the manufacturer. Optionally, the bottom end 204 of the strip 200 is inserted into the oil reservoir 14 before the tube 214.

Optionally, the strip 200 comprises a bottom flange 224 adjacent to the bottom end 204 of the strip 200. The bottom flange 224 is preferably designed to prevent the tube 214 from contacting the sidewalls of the dipstick tube of the oil reservoir 14. The bottom flange 224 is preferably also designed to prevent the tube 214 from falling off the strip 200. Thus, the tube 214 may comprise a tube width 218 parallel to the strip width 208 and a tube thickness 220 parallel to the strip thickness 210, and the bottom flange 224 may comprise a bottom flange width 226 parallel to the strip width 208 and a bottom flange thickness 228 parallel to the strip thickness 210 and the bottom flange width 226 may be greater than the tube width 218 and the bottom flange thickness 228 may be greater than the tube thickness 220. (The bottom flange 224 is preferably integral to the strip 200 (e.g., the strip 200 and the bottom flange 224 are a single piece of plastic). Optionally, the bottom flange 224 is rounded and the aforementioned bottom flange width 226 and thickness 228 refer to the maximum width and thickness of the bottom flange 224 being larger than the maximum width 218 and thickness 220, respectively, of the tube 214.

Optionally, the system further includes a tube stop 230 comprising a tube stop slot 232 that is slid from the strip top end 202 toward the tube 214 and the strip bottom end 204. The tube stop slot 232 receives the strip 200 (meaning that the strip 200 passes through the tube stop slot 232). The tube stop slot 232 extends the full length of the tube stop 230. (The tube stop length is parallel to the strip length 206). The tube stop slot 232 is preferably located in the center of the tube stop width 236, discussed below. Optionally, the tube stop 230 comprises a fastener configured to attach the tube stop 230 to the strip 200. For example, similar to a cable tie, the strip 200 may comprise a plurality of teeth 212 spaced along the strip length 206 and the tube stop fastener may comprise a ratchet 234 configured to engage the plurality of teeth 212 and allow the tube stop 230 to travel from the strip top end 202 towards the tube 214 and the bottom end 204 of the strip 200. The ratchet 234 of the tube stop 230 is configured to prevent the tube stop 230 from traveling in the reverse direction (towards the top end 202 of the strip 200) at least without a user manipulating the ratchet 234 similar to a reusable cable tie. Optionally, the tube stop 230 comprises a tube stop width 236 parallel to the strip width 208 and a tube stop thickness 238 parallel to the strip thickness 210 and the tube stop width 236 (more particularly the maximum width of the tube stop 230) is greater than the tube width 218 (more particularly the maximum width of the tube 214) and the tube stop thickness 238 (more particularly the maximum thickness of the tube stop 230) is greater than the tube thickness 220 (more particularly the maximum thickness of the tube 214). Optionally, the tube 214 is generally cylindrical in shape (so that the tube width 218 and thicknesses 220 are the tube diameter) and the tube stop 230 comprises a flat bottom end 240 configured to contact the tube 214 and a rounded top end 242 and the tube stop 230 tapers from the tube stop bottom end 240 to the tube stop top end 242. The tube stop 230 preferably functions as the top stop of the tube 214 and also prevents the tube 214 from contacting the sidewalls of the dipstick tube of the oil reservoir 14. Thus, the tube stop 230 and the bottom flange 224 fasten the tube 214 to the strip 200 by sandwiching and thus immobilizing the tube 214.

Optionally, after fastening the tube stop 230 onto the strip 200, the method includes sliding a top flange 244 having a slot 248 from the strip top end 202 toward the tube 214 prior to inserting the strip 200 into the oil reservoir 14. The top flange slot 248 receives the strip 200. The top flange slot 248 extends the full length of the top flange 244. (The top flange length is parallel to the strip length 206). The top flange slot 248 is preferably located in the center of the top flange width 250. Optionally, the top flange 244 includes side holes 249 to save on material.

A purpose of the top flange 244 is to provide the user an indication of how far to insert the strip 200 into the oil reservoir 14. Thus, the top end of the strip 202 and the top flange 244 are not inserted in the oil reservoir 14. Instead, the top flange 244 preferably contacts the top of the oil reservoir 14. Thus, it will also be understood that since the bottom flange 224, tube 214 and tube stop 230 but not the top flange 244 are designed to fit into the oil reservoir 14, e.g., the top of the dipstick tube, the top flange width 250 is greater than the bottom flange width 226, the tube width 218 and the tube stop width 236 and the top flange thickness 252 is greater than the bottom flange thickness 228, the tube thickness 220 and the tube top stop thickness 238.

Optionally, similar to the tube stop 230, the top flange 244 comprises a ratchet 246 configured to engage the plurality of teeth 212 and allow the top flange 244 to travel towards the bottom end 204 of the strip 200.

Optionally, the user places his fingers between the top end 202 of the strip 200 and the top flange 244 while inserting the strip 200 into the oil reservoir 14 so that he doesn't move the top flange 244 toward the strip bottom end 204. Optionally, oil in the oil reservoir 14 is configured to absorb to the tube 214 at ambient temperature. Optionally, oil in the oil reservoir 14 is configured to absorb to the tube 214 independent of the oil temperature. Optionally, the strip top end 202 is tapered to allow the user to easily slide on the tube stop 230 and top flange 244.

Exemplary dimension of the strip length 206 are from about 12 inches to about 28 inches, exemplary dimensions of the strip width 208 are from about 0.156 inches to about 0.187 inches, and exemplary dimensions of the strip thickness 210 is about 0.055 inches. Exemplary dimensions of the bottom flange 224 and tube stop 230 are from about 0.25 inches to about 0.281 inches in width (widths are again denoted by numerals 226 and 236) by from about 0.25 inches to about 0.281 inches in thickness (thicknesses are denoted by the numerals 228 and 238) by about 0.25 inches in length (the lengths are not numbered in the drawings but are parallel to the strip length 206). Exemplary dimensions of the top flange 244 are about 1 inch wide (denoted by the numeral 250) by about 0.312 inches thick (denoted by the numeral 252) by about 0.25 inches in length (length is not numbered in the drawings but is parallel to the strip length 206). Exemplary dimensions of the tube width and thickness 218 and 220 (more particularly outer diameter) are from about 0.187 inches to about 0.210 inches. It will be understood that the aforementioned dimensions are merely for illustrations purposes and is not intended to limit the scope of the present disclosure.

The Embodiments of FIGS. 20-26

FIGS. 20-26 illustrate yet another embodiment of a strip 300 that is used to visualize oil level in oil reservoir. FIGS. 20-26 are CAD drawings drawn to scale. However, it will be appreciated that other dimensions are possible.

Figure 20:
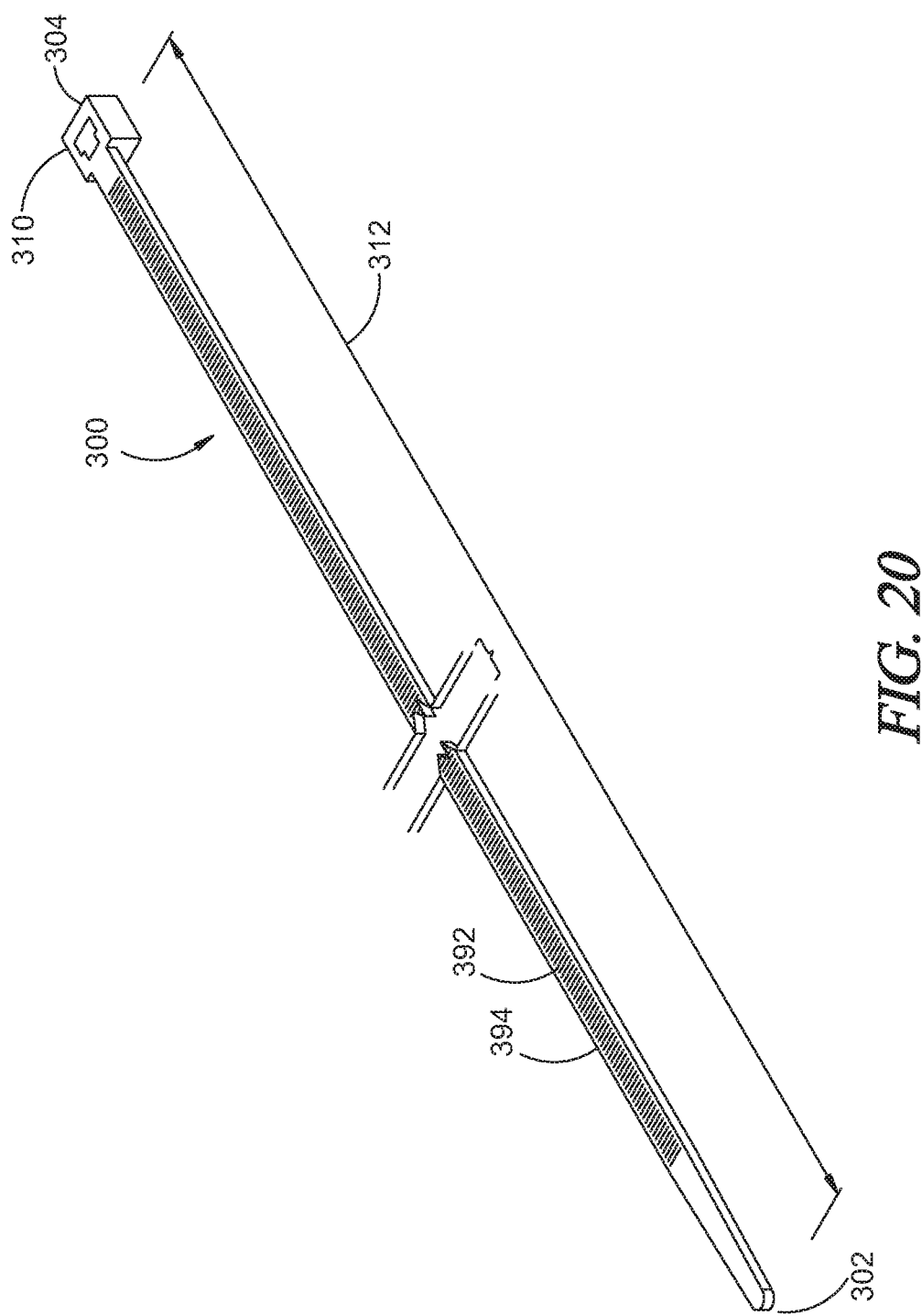
FIG. 20 illustrates a front perspective view of a strip of another embodiment of the present invention.

In particular, FIG. 20 illustrates a front perspective view of the starting material for the strip 300, namely a cable tie with a tapered bottom end 302, a top end 304 comprising a ratchet 310 opposite the bottom end 302, a strip length 312 extending from the strip bottom end 302 to the ratchet 310, a plurality of teeth 392 located on the strip front surface 394 along the length. Optionally, the cable tie has a length of about 11 inches to about 34 inches.

Figure 21:
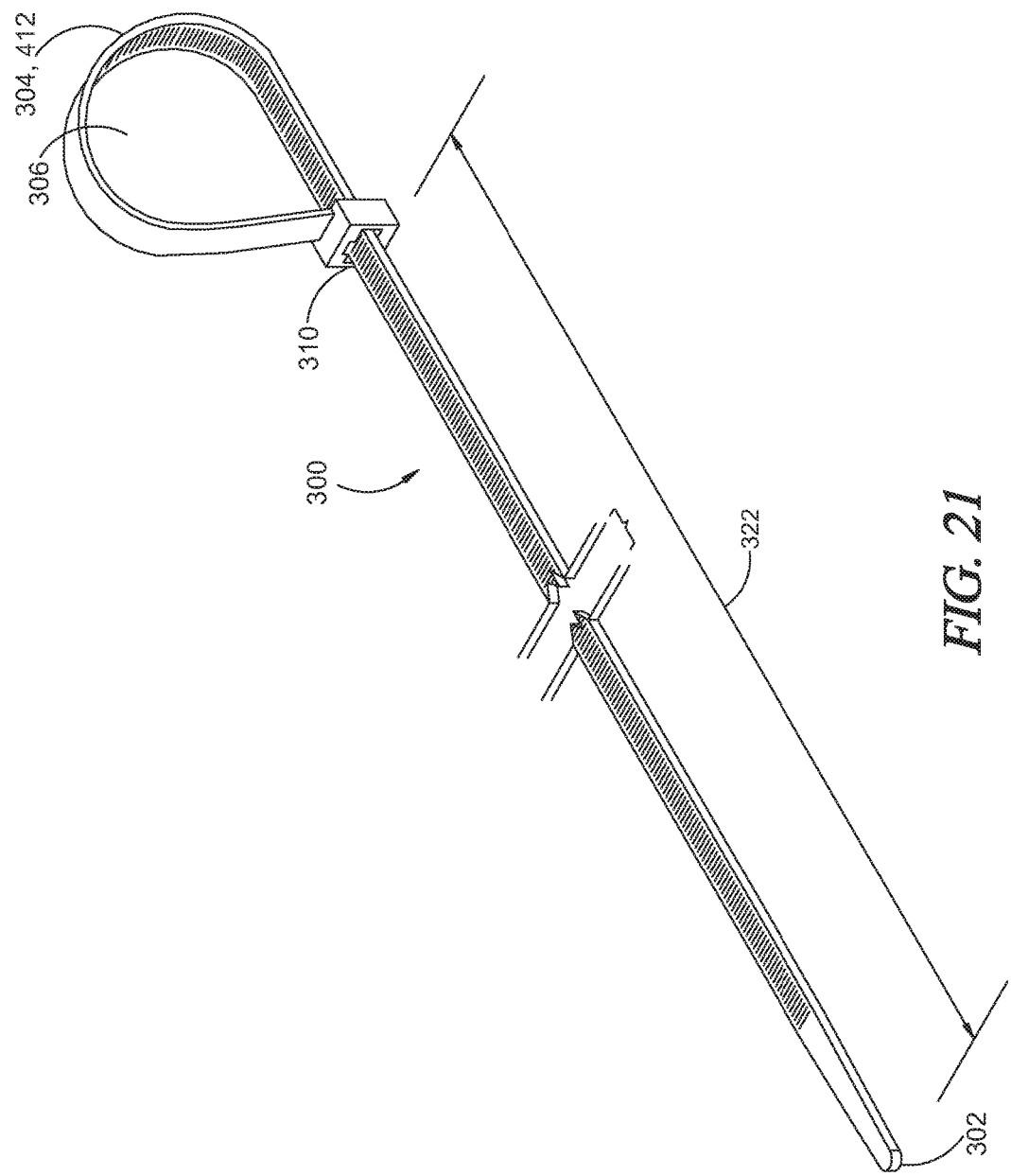
FIG. 21 illustrates a front perspective view of the strip of FIG. 20 after moving the ratchet through the strip bottom end and then upwardly to create a loop at the top end of the strip.

FIG. 21 illustrates a front perspective view of the strip 300 of FIG. 20 after moving the ratchet 310 through the strip bottom end 302 and then upwardly to create a loop 306 at the top end of the strip and create an adjustable strip lower portion length 322 below the loop 306. In other words, as with the case with any cable tie, the distance 322 between the strip bottom end 302 and the ratchet 310 is adjustable in one direction—i.e., by moving the ratchet 310 upwardly and thereby decreasing the size of the loop 306. The loop 306 is intentionally set oversized so that the user may move the ratchet 310 forwardly to line up with his/her dipstick as will be later described with respect to FIG. 25. The strip top end 304 is now the loop apex 412 as shown in FIG. 21

Figure 22:
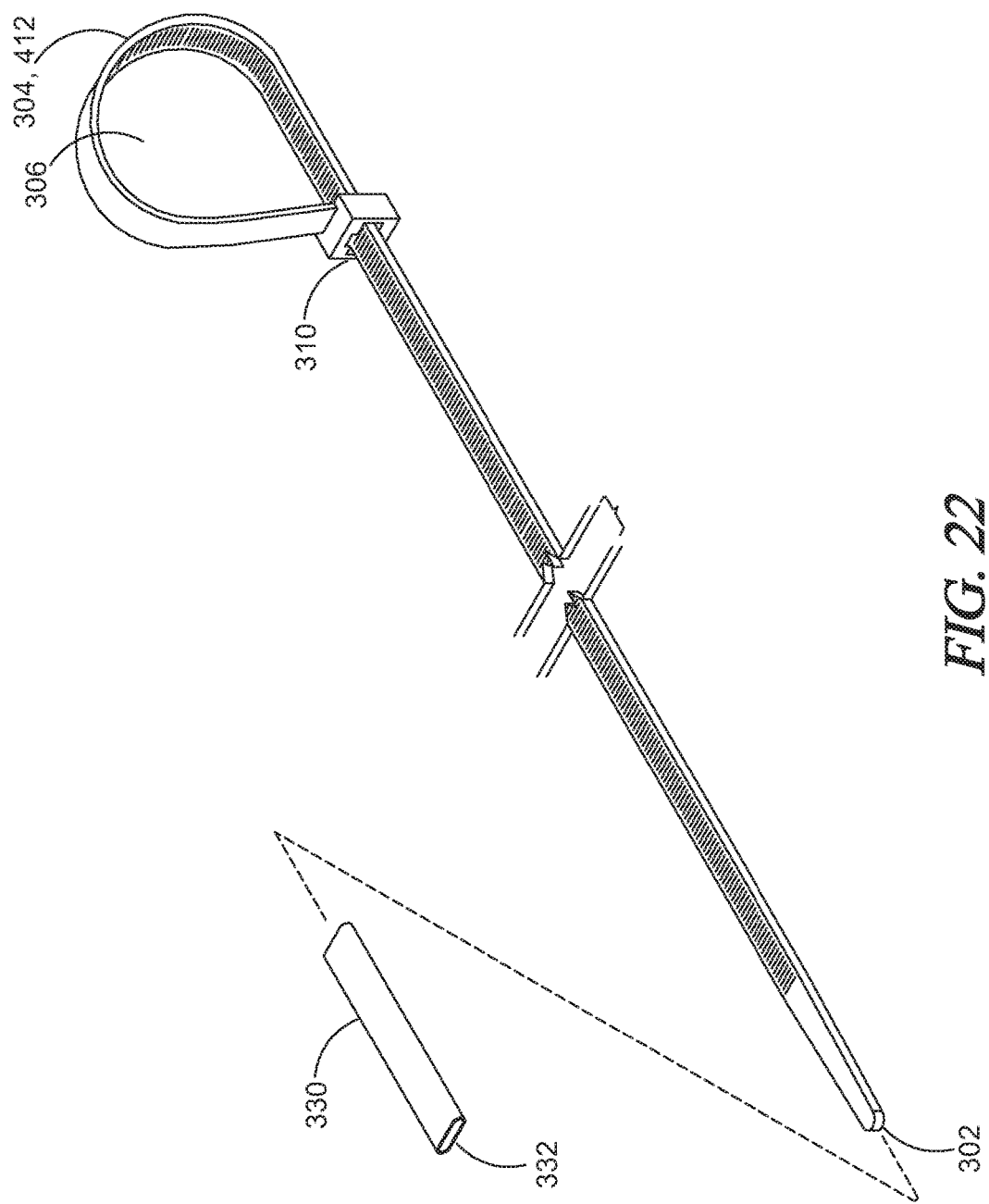
FIG. 22 illustrates a front perspective view of a tube that will be placed through the bottom end of the strip of FIG. 21.

FIG. 22 illustrates a front perspective view of a flattened tube 330 with a hollow tube interior 332 that will be placed through the strip bottom end 302 of FIG. 21. The tube 330 is preferably comprised of an oil absorbent cellulosic material (e.g., a paper-based material) as previously described.

Figure 23:
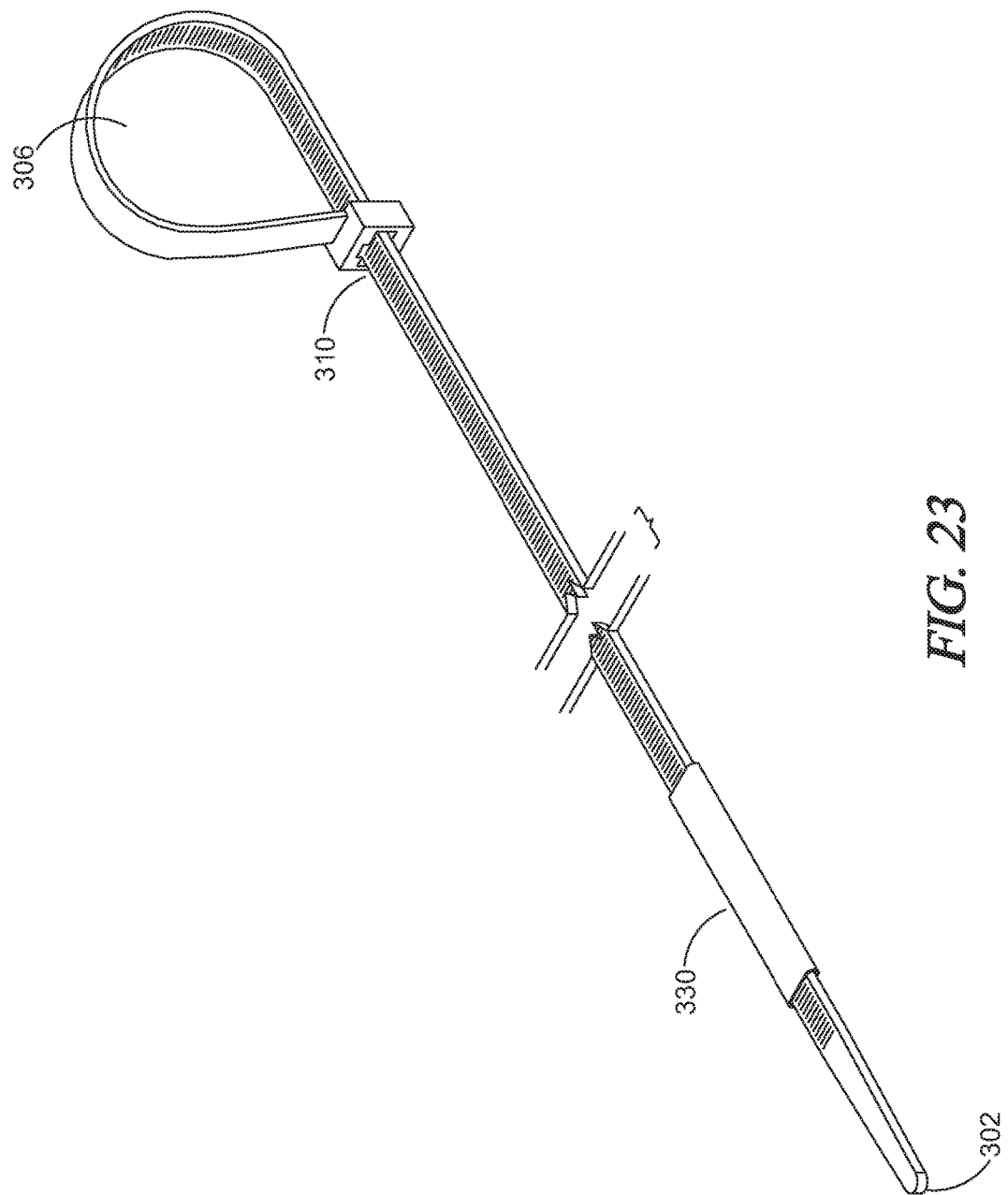
FIG. 23 illustrates a front perspective view of the strip of FIG. 22 after the tube has been place through the bottom end of the strip.
Figure 24A:
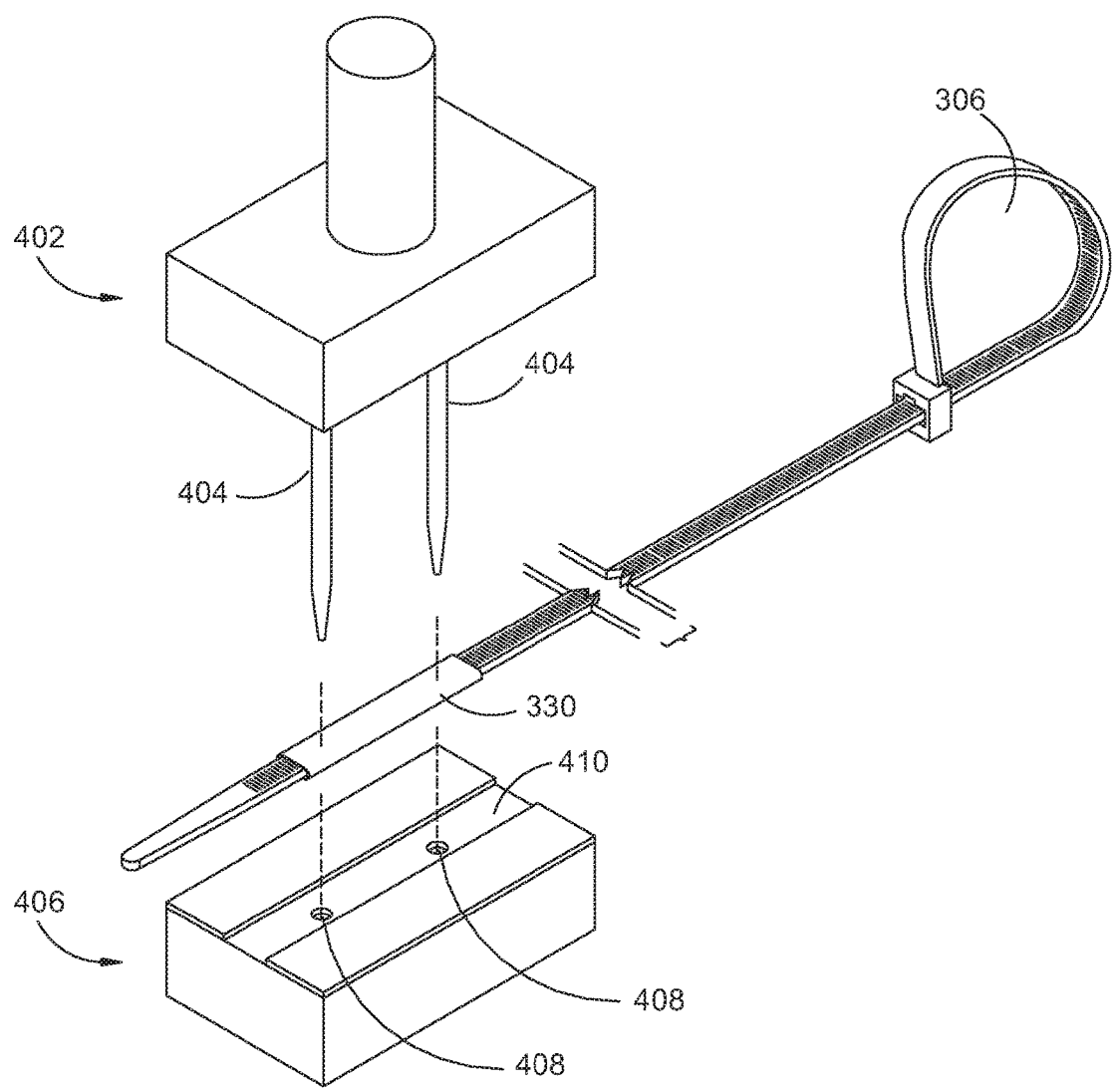
FIG. 24A illustrates a front perspective view of the strip of FIG. 23 before piercing the tube/upsetting the strip in two locations with a tapered punch.
Figure 24B:
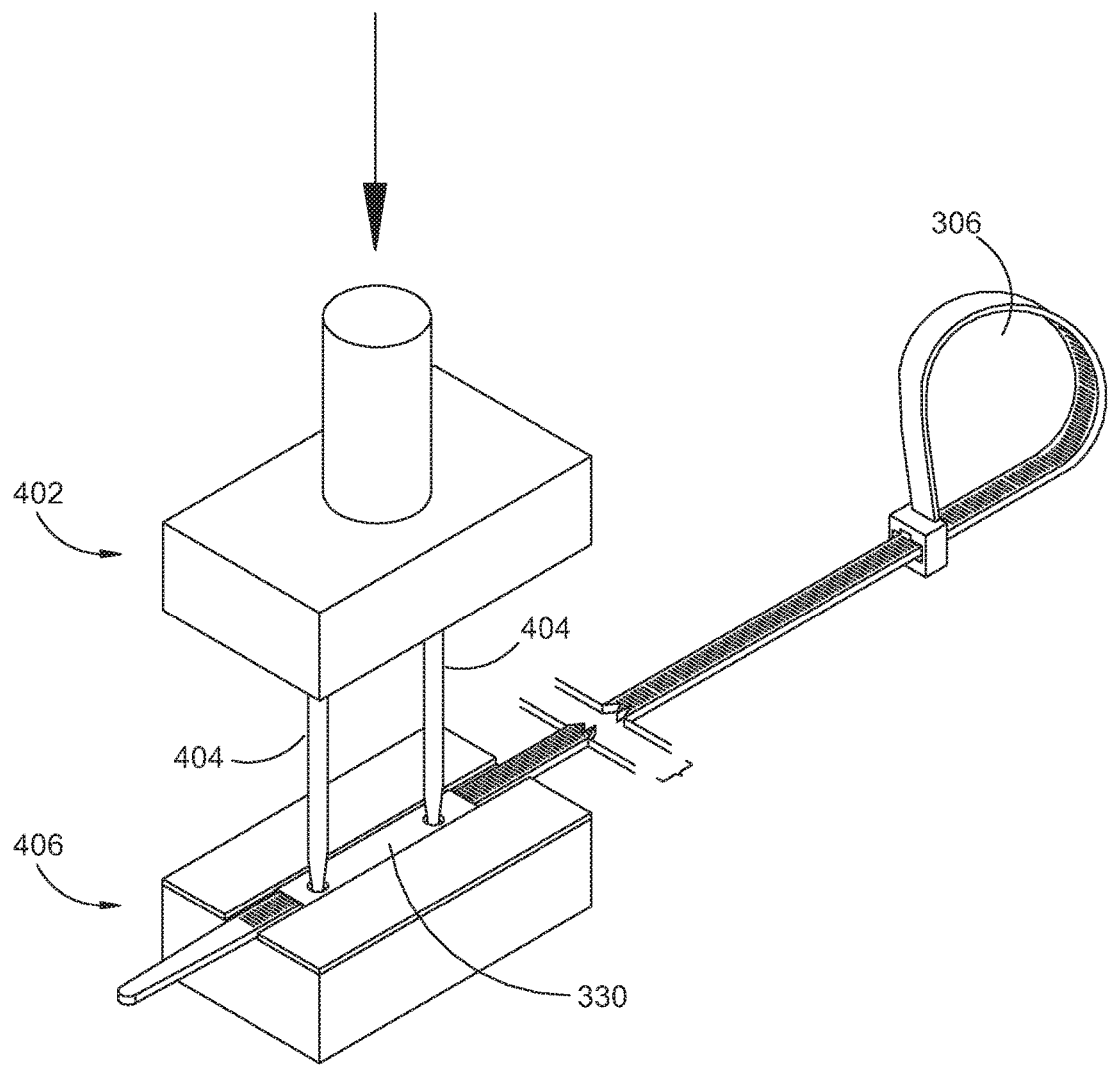
FIG. 24B illustrates a front perspective view of the strip of FIG. 24A while piercing the tube/upsetting the strip in two locations with a tapered punch.
Figure 24C:
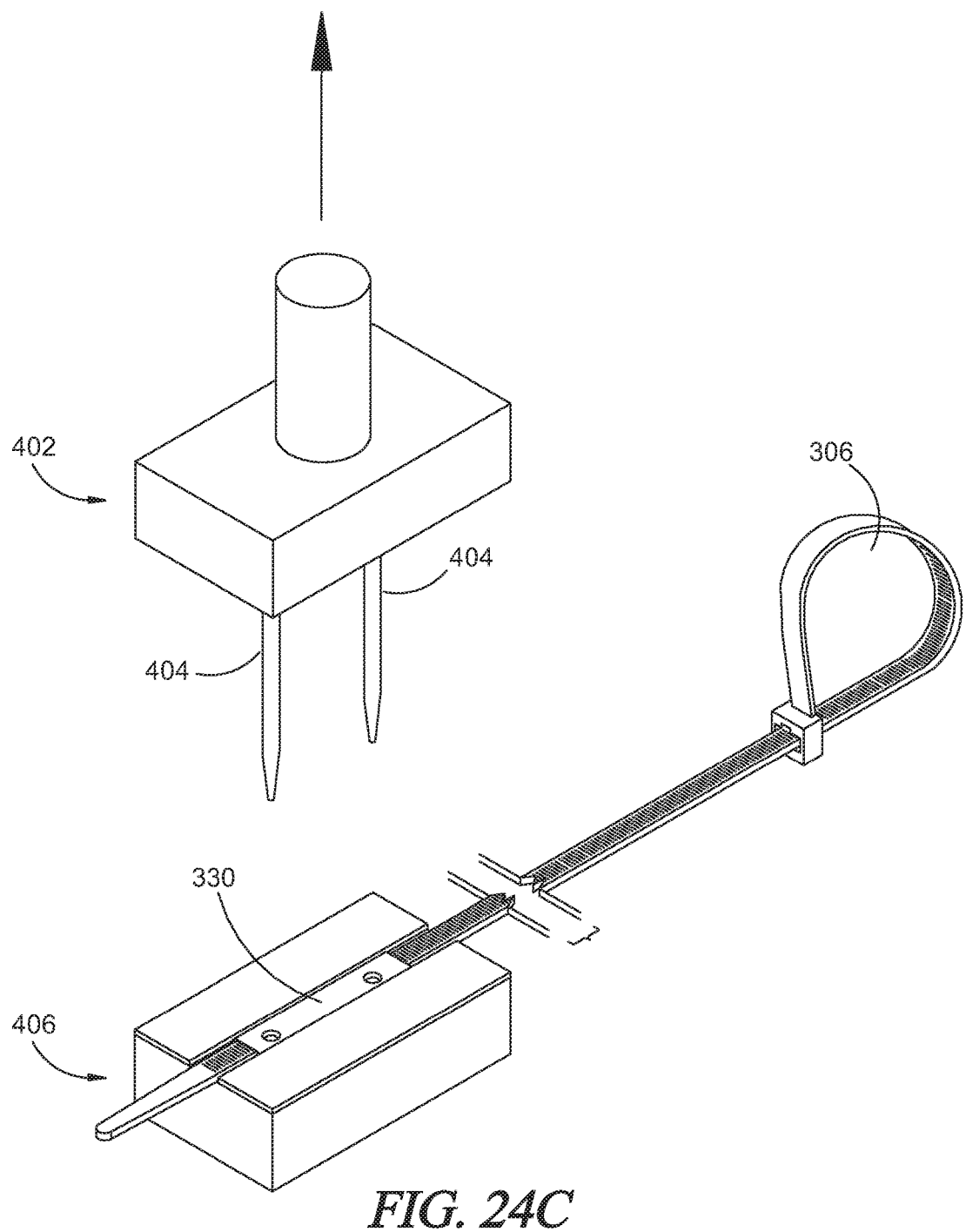
FIG. 24C illustrates a front perspective view of the strip of FIG. 24B after piercing the tube/upsetting the strip in two locations with a tapered punch.
Figure 24D:
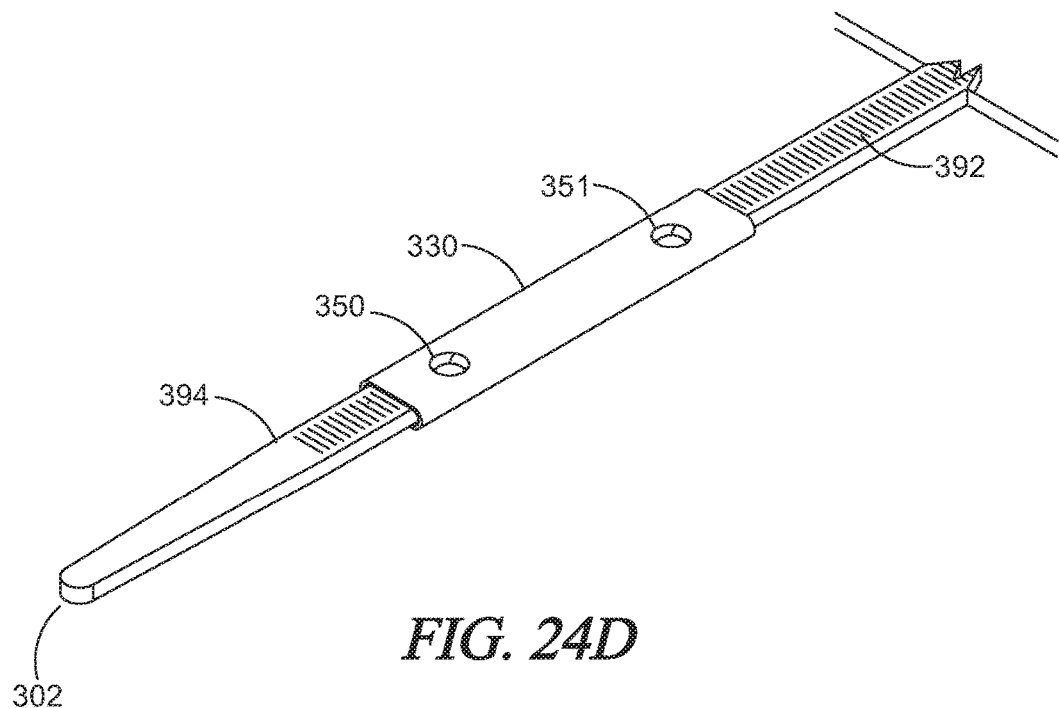
FIG. 24D illustrates a front perspective view of the lower portion of the strip of FIG. 24C.
Figure 24E:
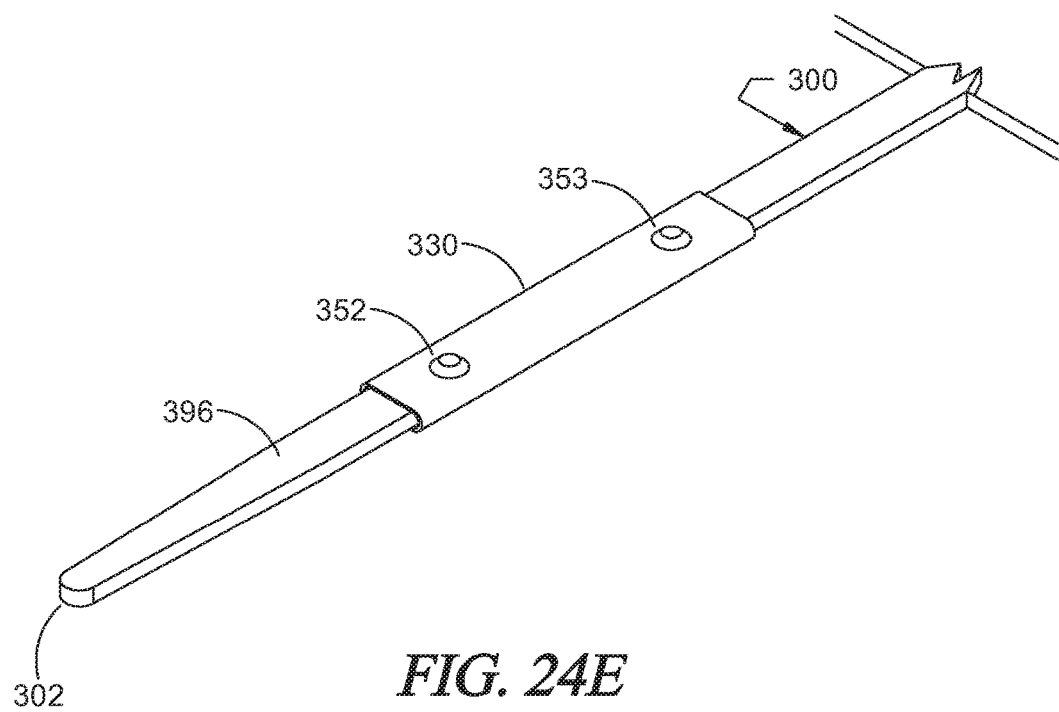
FIG. 24E illustrates a rear perspective view of the lower portion of the strip of FIG. 24C.
Figure 24F:
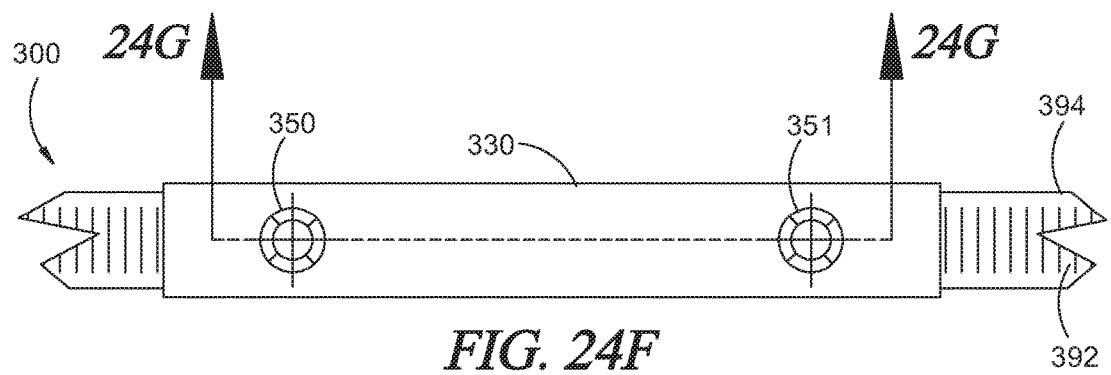
FIG. 24F illustrates a front plan view of the lower portion of the strip of FIG. 24D.
Figure 24G:
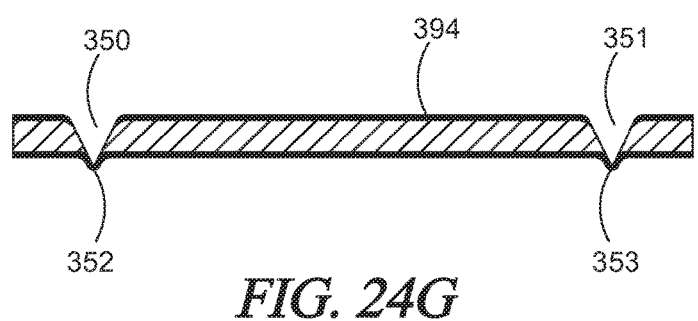
FIG. 24G illustrates a side sectional view of the strip of FIG. 24F taken along line 24G-24G.

FIG. 23 illustrates a front perspective view of the strip 300 of FIG. 22 after the tube 330 has been placed through the strip bottom end 302.

FIGS. 24-A-24G show one exemplary method of attaching the tube 330 to the strip 300 above the strip bottom end 302. FIG. 24A illustrates a front perspective view of the strip 300 of FIG. 23 before piercing the tube/upsetting the strip 300 in two locations with a tapered punch 404 and tapered die 408 combination. The tapered punch 404 is mounted in punch press top die 402. The tapered die 408 is machined into punch press bottom die 406. Punch press top die 402 and punch press bottom die 406 can be mounted into a multitude of conventional hand or machine leverage presses. FIG. 24B illustrates a front perspective view of the strip 300 of FIG. 24A while piercing the tube/upsetting the strip in two locations with a tapered punch 404. In FIG. 24B, the strip 300 is placed in the strip/tube locating pocket denominated by numeral 410 in FIG. 24A. FIG. 24C illustrates a front perspective view of the strip 300 of FIG. 24B after piercing the tube/upsetting the strip 300 in two locations with a tapered punch 404. FIG. 24D illustrates a front perspective view of the lower portion of the strip 300 of FIG. 24C. As shown in FIG. 24D, the piercing creates a lower dimple 350 and upper dimple 351 on the front surface of the strip 394. FIG. 24E illustrates a rear perspective view of the lower portion of the strip 300 of FIG. 24C. As shown in FIG. 24E, the upsetting creates a lower bump 352 and upper bump 353 on the strip rear surface 396, with the lower bump 352 being directly behind the lower dimple 350 and the upper bump 353 being directly behind the upper dimple 351. FIG. 24F illustrates a front plan view of the lower portion of the strip 300 of FIG. 24D. FIG. 24G illustrates a side sectional view of the strip of FIG. 24F taken along line 24G-24G.

Figure 25:
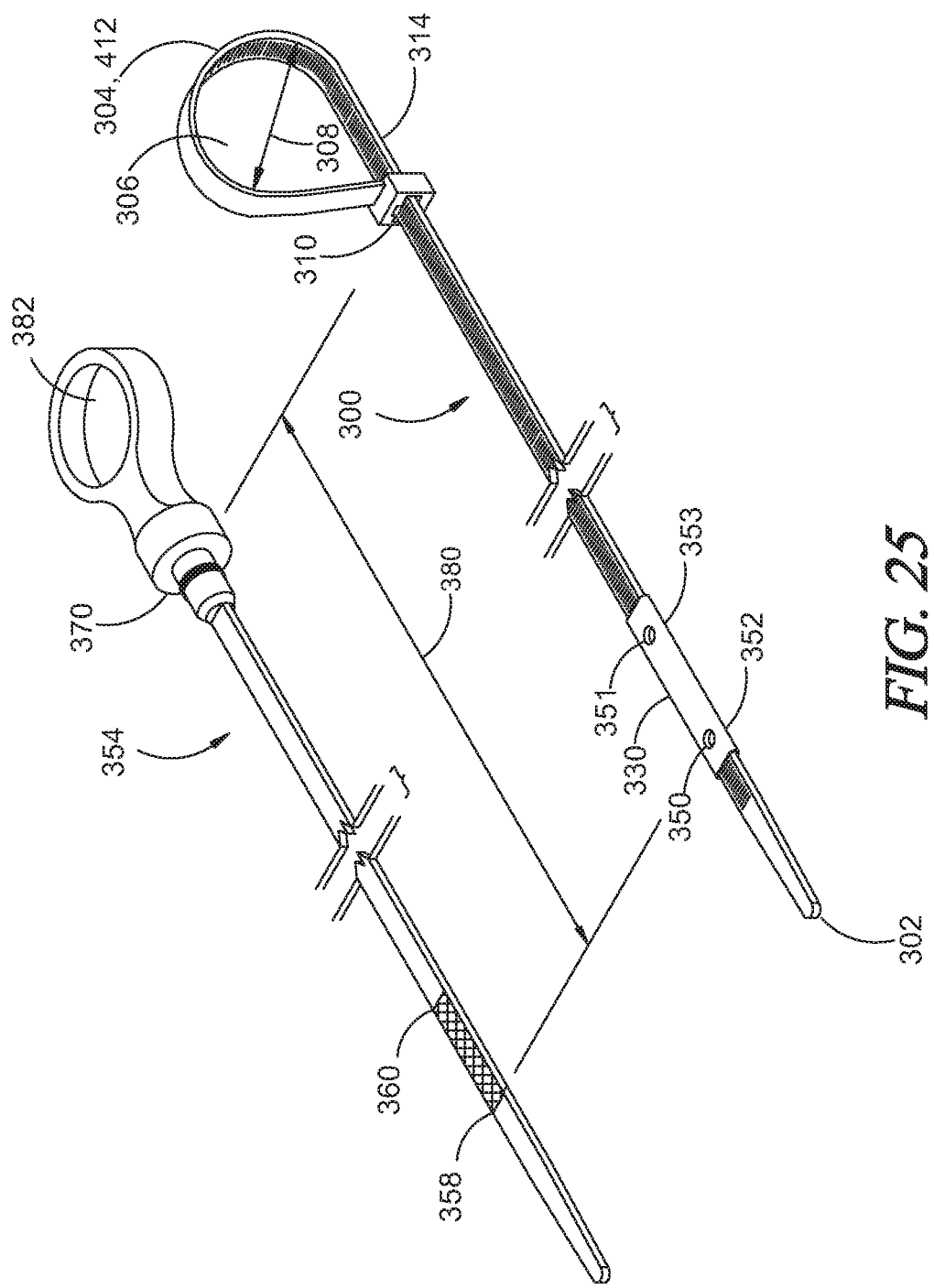
FIG. 25 illustrates a top perspective view of the strip of FIG. 24C laid next to a conventional dipstick; as compared to FIG. 21, the diameter of the loop of the strip of FIG. 25 is smaller because the user has moved the ratchet upwardly so that the ratchet is aligned with the dipstick stop and the dipstick low reading is aligned with the lower dimple.

FIG. 25 illustrates how the upper dimple 351 on strip front surface 394 (or the upper bump 353 on strip rear surface 396) can be used to serve as the oil full reading and the lower dimple 350 on strip front surface 394 (or the lower bump 352 on strip rear surface 396) can be used to serve as the oil low reading. FIG. 25 illustrates how the user will lay the strip 300 of FIG. 24C next to a conventional dipstick 354. The user then aligns with the dipstick low reading 358 with the lower dimple 350. (Preferably, the dipstick full reading 360 also aligns the upper dimple 351. However, the distance between the low and full oil readings on dipsticks varies by engine manufacturer so the upper dimple 351 will not always fully align with the dipstick full reading 360. The user has the option to mark the full reading on the tube 330 by marking on the tube himself/herself.). The user then moves the ratchet 310 upwardly so that the ratchet 310 is aligned with the dipstick stop 370, and as a result, the diameter of the loop 308 of the strip 300 of FIG. 25 decreases in size, the distance between the lower dimple 350 and ratchet 310 increases, matching the distance 380 between the user dipstick low reading 358 and user dipstick stop 370, and the overall length of the strip increases. The user may now use the strip of FIG. 25 as his/her replacement dipstick and may use the lower dimple 350 on strip front surface 394 (or the lower bump 352 on strip rear surface 396) to serve as the low oil reading and the upper dimple 351 on strip front surface 394 (or the upper bump 353 on strip rear surface 396) to serve as the oil full reading, and ratchet 310 to mimic the dipstick stop 370. The loop diameter 308 of loop 306 prevents strip 300 from accidentally falling into the oil reservoir.

More particularly, the dipstick of FIGS. 20-25 may be used in a method that includes: a) providing an engine comprising an oil reservoir configured to hold oil, the oil reservoir comprising a dipstick configured to measure oil level in the oil reservoir, as previously shown and described; b) removing the dipstick from the oil reservoir, as previously described; c) providing the strip 300 of FIG. 25; d) inserting at least the bottom end 302 of the strip 300 and the tube 330 into the oil reservoir (preferably until the ratchet 310 contacts the top of the dipstick tube); and e) absorbing oil from the oil reservoir to the tube 330 to provide a stain on the tube 330 visible to the naked eye. The user may then determine to add oil if the stain is at or near the lower dimple 350 (which serves as the low oil indicia) and decide not to add oil if the stain is at or near the upper dimple 351 (which serves as the full oil indicia). Optionally, the user places his fingers inside the loop 306 (similarly to finger positions inside user dipstick loop 382) during steps d) and step e), and specifically the user may grasp the location on the strip denominated by numeral 314 in FIG. 25

Figure 26A:
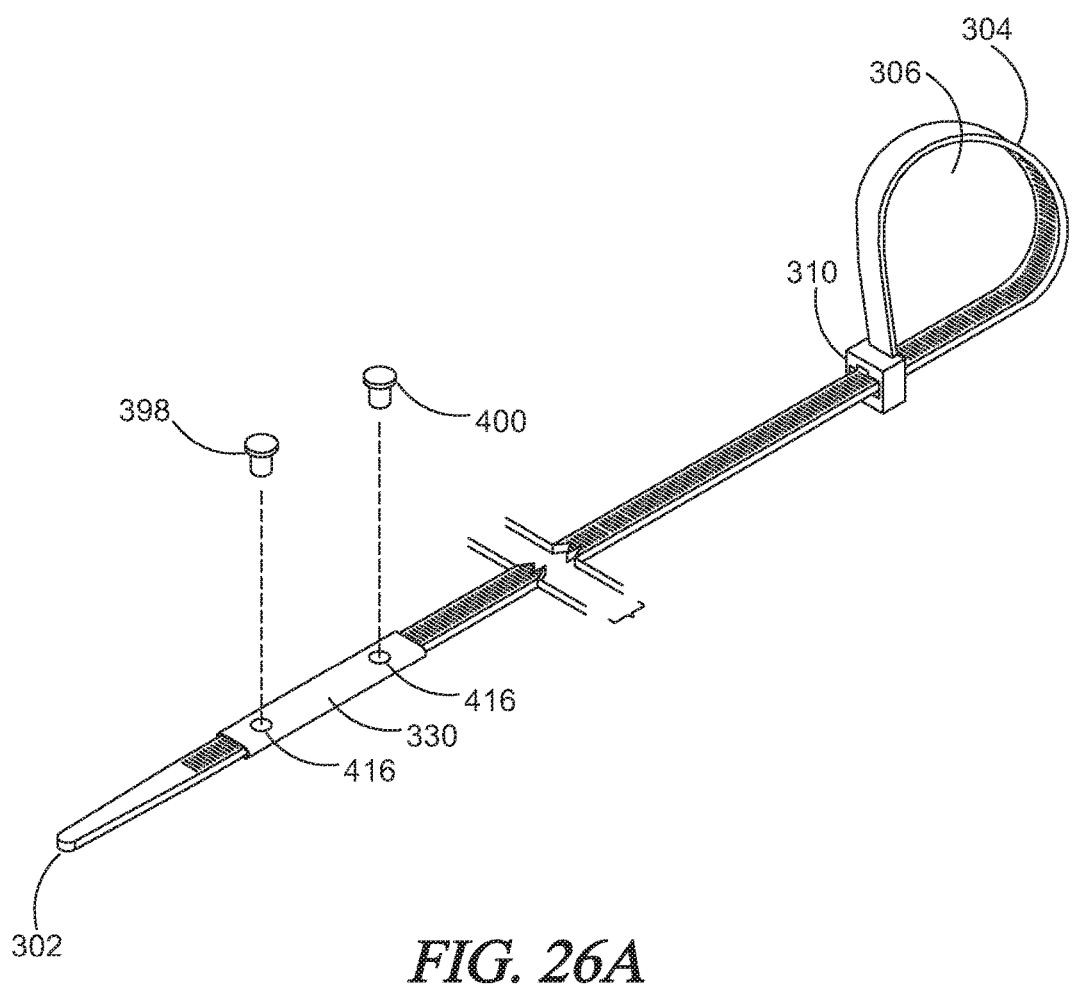
FIG. 26A illustrates a top perspective view of the strip and tube of FIG. 23 before rivets are being used to attach the tube to the strip.
Figure 26B:
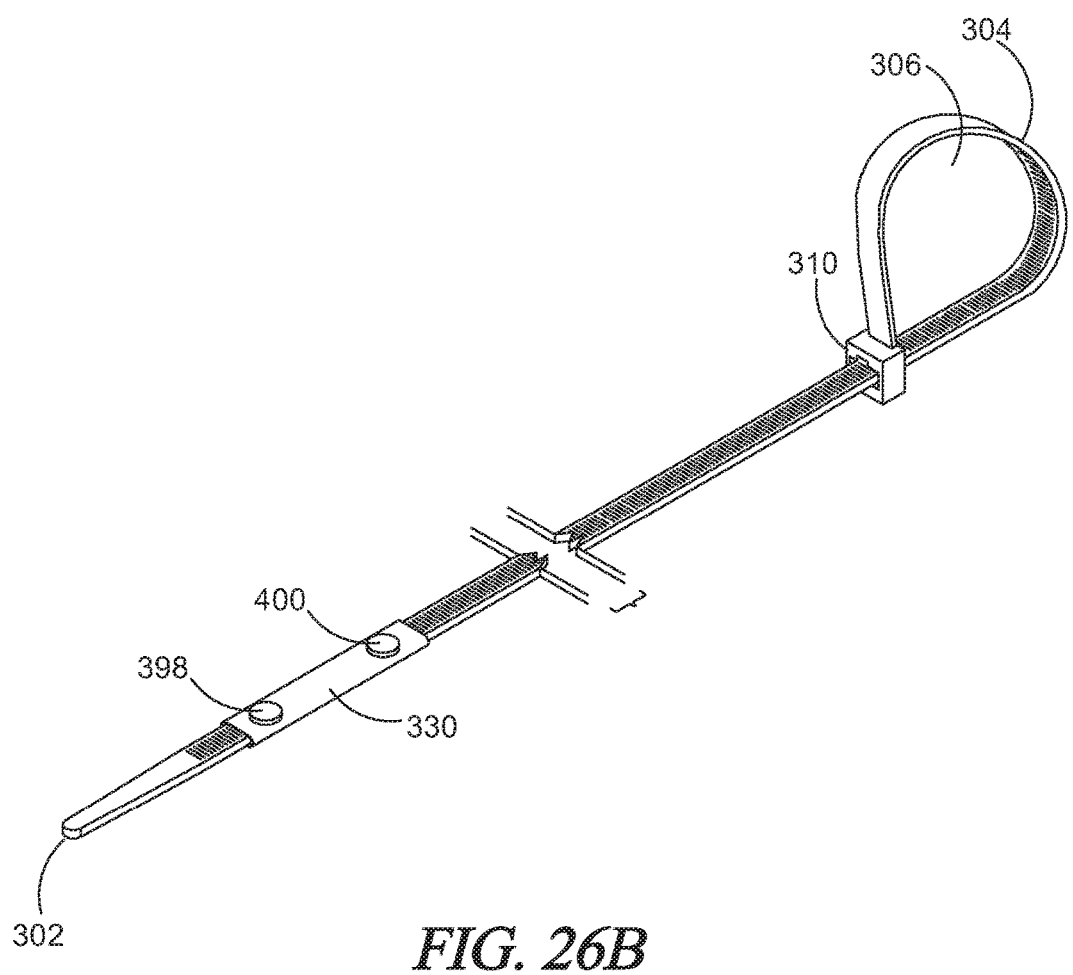
FIG. 26B illustrates a top perspective view of the strip and tube of FIG. 26A after rivets have been used to attach the tube to the strip.

As opposed to a piercing/upsetting operation, any other suitable method may be used to attach the tube 330 to the strip 300. Preferably, a fastener is used. For example, an alternate fastener, namely rivets 398, 400 are shown in FIGS. 26A and 26B. FIG. 26A illustrates a top perspective view of the strip 300 and tube 330 of FIG. 23 before rivets 398, 400 are being passed through punched/drilled holes 416 through the tube 330 and strip 300 to attach the tube 330 to the strip 300. FIG. 26B illustrates a top perspective view of the strip 300 and tube 330 of FIG. 26 after rivets 398, 400 have been used to attach the tube 330 to the strip 300. The advantage of the rivets 398, 400 (as well as the previously described piercing/upsetting operation) is that the attachment mechanism also may be used as indicia for low oil and full oil).

Preferably, the strip 300 is comprised of a heat-resistant, non-oil absorbent material, e.g. plastic. Preferably, oil in the oil reservoir is configured to absorb to the tube 330 independent of the oil temperature.

Due to the fact that the strip 300 is preferably formed from a plastic cable tie (with a thickness of between for example 0.050 and 0.080 inches), the strip is highly flexible, allowing the strip to navigate any turns in the dipstick tube. Additionally, the flattened nature of the tube creates a low profile, which also allows the strip to navigate any turns in the dipstick tube.

| Part List for FIGS. 20-26 | |
|---|---|
| strip | 300 |
| strip bottom end | 302 |
| strip top end | 304 |
| loop | 306 |
| loop diameter | 308 |
| strip length | 312 |
| ratchet/bottom of loop/stop | 310 |
| user grasp point | 314 |
| distance 322 between the strip bottom end 302 and the ratchet 310 | 322 |
| tube | 330 |
| tube interior | 332 |
| lower dimple | 350 |
| upper dimple | 351 |
| lower bump | 352 |
| upper bump | 353 |
| user dipstick | 354 |
| user dipstick low reading | 358 |
| user dipstick full reading | 360 |

-continued

| Part List for FIGS. 20-26 | |
|---|---|
| user dipstick stop | 370 |
| distance between 358 and 370, which matches distance between 350 and 310 | 380 |
| user dipstick loop | 382 |
| strip teeth | 392 |
| strip front surface | 394 |
| strip rear surface | 396 |
| lower fastener/rivet | 398 |
| upper fastener/rivet | 400 |
| punch press top die | 402 |
| tapered punch | 404 |
| punch press bottom die | 406 |
| tapered die | 408 |
| strip/tube locating pocket | 410 |
| loop apex | 412 |
| punched/drilled hole | 416 |

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A method of using an oil level visualization system comprising:
  a) providing an engine comprising an oil reservoir configured to hold oil, the oil reservoir comprising a dipstick configured to measure oil level in the oil reservoir;
  b) removing the dipstick from the oil reservoir;
  c) providing a strip having a top end comprising a loop, a bottom end, a length extending from the top end to the bottom end, a width perpendicular to the length, and a thickness perpendicular to the width and the length, wherein a tube located below the loop is attached to the strip, the tube comprised of an oil absorbent material and comprising a hollow interior receiving the strip;
  d) inserting at least the bottom end of the strip and the tube into the oil reservoir; and
  e) absorbing oil from the oil reservoir to the tube to provide a stain on the tube visible to the naked eye.

2. The method of claim 1, wherein the strip is comprised of a heat-resistant, non-oil absorbent material.

3. The method of claim 2 wherein the oil absorbent material is a cellulosic, paper-based material.

4. The method of claim 1 wherein, prior to step d) the tube comprises at least one indicia visible to the naked eye, the indicia configured to provide a reading on the oil level in the oil reservoir to a user.

5. The method of claim 4 wherein the at least one indicia comprises a lower dimple located above the strip bottom end.

6. The method of claim 5 wherein the strip comprises a front surface and a rear surface, wherein the thickness extends from the front surface to the rear surface, wherein the lower dimple is located on the front surface of the strip, and further wherein the rear surface of the strip comprises a bump located directly to the rear of the lower dimple.

7. The method of claim 5 wherein the at least one indicia further comprises an upper dimple located above the lower dimple.

8. The method of claim 1, wherein, step d) comprises inserting the bottom end of the strip before the tube into the oil reservoir.

9. The method of claim 1 wherein the strip is the form of a cable tie comprising a plurality of teeth spaced along the length of the strip and a ratchet configured to engage the plurality of teeth, the ratchet forming a bottom end of the loop and located above the tube.

10. The method of claim 9 wherein the loop comprises an adjustable size and further wherein moving the ratchet upwardly reduces the size of the loop and increases the distance between the ratchet and the strip bottom end.

11. The method of claim 10 wherein, prior to step d) the tube comprises at least one indicia visible to the naked eye, the at least one indicia configured to provide a reading on the oil level in the oil reservoir to a user.

12. The method of claim 11 wherein the dipstick further comprises a loop, a dipstick stop below the loop, a low reading below the dipstick stop and the method further comprises, before step d), laying the strip next to the dipstick so that the low reading is aligned with the at least one indicia and then moving the ratchet forwardly so that the ratchet is aligned with the dipstick stop.

13. The method of claim 12 wherein the at least one indicia is in the form of a dimple.

14. The method of claim 1 wherein the tube is attached to the strip by a fastener at a fixed location along the strip length above the strip bottom end.

15. The method of claim 1 wherein the tube is flattened.

16. The method of claim 1 wherein the user places his fingers inside the loop during steps d) and step e).

17. An oil level visualization system comprising:
a strip comprised of a heat-resistant, non-oil absorbent material and having a top end comprising a loop, a bottom end, a length extending from the top end to the bottom end, a width perpendicular to the length, and a thickness perpendicular to the width and the length,
wherein a tube located below the loop is attached to the strip, the tube comprised of an oil absorbent material and comprising a hollow interior receiving the strip, and
further wherein the strip is the form of a cable tie comprising a plurality of teeth spaced along the length of the strip and a ratchet configured to engage the plurality of teeth, the ratchet forming a bottom end of the loop and located above the tube.

18. The system of claim 17 wherein the oil absorbent material is a cellulosic, paper-based material.

19. The system of claim 17 wherein the tube comprises at least one indicia visible to the naked eye.

20. The system of claim 17 wherein the tube is attached to the strip at a fixed location along the strip length above the strip bottom end, wherein the loop comprises an adjustable size and further wherein moving the ratchet upwardly reduces the size of the loop and increases the length of the strip.

* * * * *